United States Patent
Hu et al.

(10) Patent No.: US 10,687,899 B1
(45) Date of Patent: Jun. 23, 2020

(54) BONE MODEL CORRECTION ANGLE DETERMINATION

(71) Applicant: Smith & Nephew, Inc., Memphis, TN (US)

(72) Inventors: Yangqiu Hu, Lewis Center, OH (US); Mohammed Rahman, Cordova, TN (US); Stephen Mirdo, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 411 days.

(21) Appl. No.: 15/641,921

(22) Filed: Jul. 5, 2017

Related U.S. Application Data

(60) Provisional application No. 62/358,328, filed on Jul. 5, 2016.

(51) Int. Cl.
| | |
|---|---|
| *G06F 30/10* | (2020.01) |
| *A61B 34/10* | (2016.01) |
| *G16H 50/50* | (2018.01) |
| *G06F 30/23* | (2020.01) |

(52) U.S. Cl.
CPC .............. *A61B 34/10* (2016.02); *G16H 50/50* (2018.01); *A61B 2034/105* (2016.02); *G06F 30/10* (2020.01); *G06F 30/23* (2020.01)

(58) Field of Classification Search
CPC ..................... G06T 7/0012; G06T 7/60; G06T 2207/10116; G06T 2207/20104; A61B 34/10; A61B 6/505; G06F 30/10
USPC .................................. 703/2, 5; 382/173, 254
See application file for complete search history.

(56) References Cited

U.S. PATENT DOCUMENTS

| | | | | |
|---|---|---|---|---|
| 6,851,851 | B2 * | 2/2005 | Smith .................. | A61B 6/0457 378/167 |
| 8,275,201 | B2 * | 9/2012 | Rangwala ............ | G06T 7/0012 382/128 |
| 10,136,869 | B2 * | 11/2018 | Behrooz ................ | A61B 6/505 |
| 10,154,884 | B2 * | 12/2018 | Kumar .................. | A61B 34/10 |
| 10,251,705 | B2 * | 4/2019 | Kumar .................. | A61B 34/10 |
| 2009/0226063 | A1 * | 9/2009 | Rangwala ............ | G06T 7/0012 382/128 |
| 2017/0273651 | A1 * | 9/2017 | Behrooz ................ | A61B 6/505 |
| 2017/0348054 | A1 * | 12/2017 | Kumar .................. | A61B 34/10 |
| 2017/0348057 | A1 * | 12/2017 | Kumar .................. | A61B 34/10 |

* cited by examiner

*Primary Examiner* — Thai Q Phan
(74) *Attorney, Agent, or Firm* — Pepper Hamilton LLP

(57) ABSTRACT

An exemplary method includes receiving information relating to a long bone, and generating a bone model representative of the long bone. The long bone includes a shaft, and the bone model includes a shaft model representative of at least a portion of the shaft. The method includes identifying a target orientation for the bone model, and generating a cropped model including at least a portion of the shaft model. The method further includes generating cylinder parameters based at least in part upon the cropped model, registering the cylinder to the cropped model, and generating registration information related to the registering. The method further includes generating a correction angle based upon the registration information, and generating a corrected model based upon the correction angle. The method may further include generating an adjusted model based upon the corrected model, and generating a surgical device using the adjusted model.

25 Claims, 13 Drawing Sheets

US 10,687,899 B1

BONE MODEL CORRECTION ANGLE DETERMINATION

CROSS-REFERENCE TO RELATED APPLICATIONS

This application claims the benefit of U.S. Provisional Application No. 62/358,328, filed on Jul. 5, 2016, which is incorporated herein by reference in its entirety.

TECHNICAL FIELD

The present disclosure generally relates to determining a correction angle for a model of a long bone, and more particularly but not exclusively relates to determining a correction angle for a femoral model representative of a femur of a particular patient.

BACKGROUND

Bone models generated from medical imaging techniques are commonly used in surgical planning procedures to enable a surgeon or other user to pre-operatively generate a surgical plan and/or a patient-specific orthopedic tool. Certain techniques may require that the model be properly oriented in three-dimensional space for optimal accuracy. The orientation is often determined by visually assessing industry-recognized anatomical landmarks and features, and rotating the model to the proper orientation based upon the anatomical landmarks and features. This manual approach is subject to process inefficiencies, and the orientations determined for a single model may exhibit two types of variability. Inter-operator variability occurs when the process is performed by different operators, and intra-operator variability occurs when the process is performed by the same operator at different times. As will be appreciated, both forms of variability may adversely affect the consistency of the orientations determined for a given single model, and it may be desirable to improve the consistency of the orientations by reducing these forms of variability. Therefore, a need remains for further improvements in this technological field.

SUMMARY

An exemplary method includes receiving information relating to a long bone, and generating a bone model representative of the long bone. The long bone includes a shaft, and the bone model includes a shaft model representative of at least a portion of the shaft. The method includes identifying a target orientation for the bone model, and generating a cropped model including at least a portion of the shaft model. The method further includes generating cylinder parameters based at least in part upon the cropped model, registering the cylinder to the cropped model, and generating registration information related to the registering. The method further includes generating a correction angle based upon the registration information, and generating a corrected model based upon the correction angle. The method may further include generating an adjusted model based upon the corrected model, and generating a surgical device using the adjusted model. Further embodiments, forms, features, and aspects of the present application shall become apparent from the description and figures provided herewith.

BRIEF DESCRIPTION OF THE FIGURES

FIG. 1b is a distal illustration of the femur illustrated in FIG. 1a.

DETAILED DESCRIPTION OF ILLUSTRATIVE EMBODIMENTS

Figure 1A:
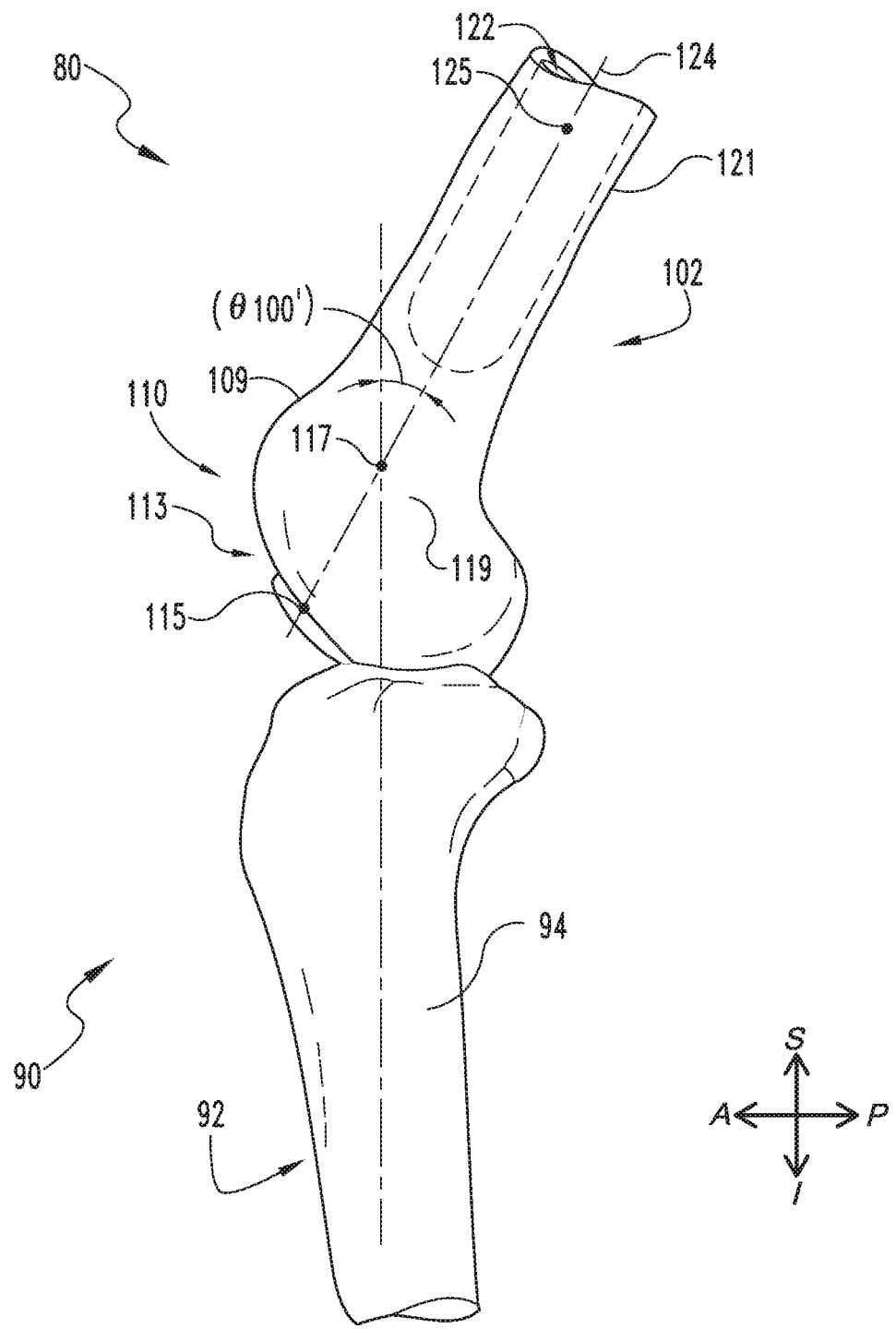
FIG. 1a is a sagittal illustration of a knee including a femur and a tibia.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1B:
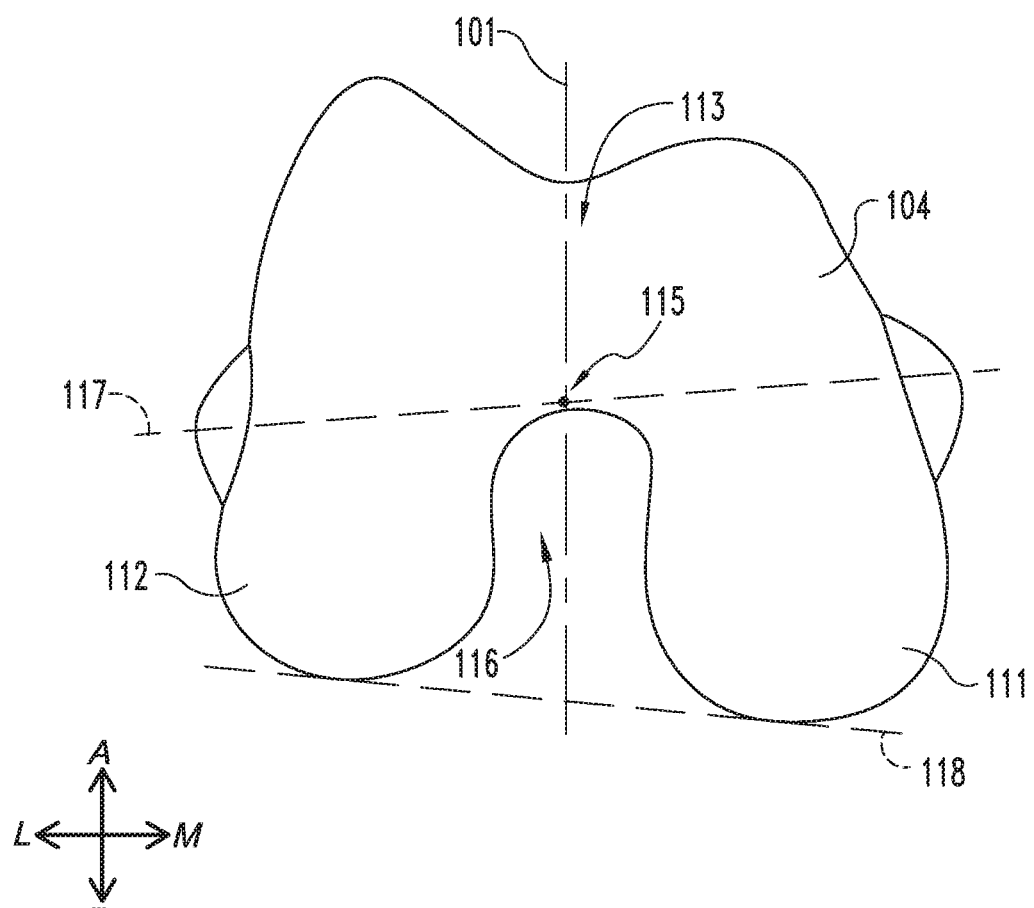

FIGS. 1a and 1b illustrate a knee 80 including a proximal portion of a tibia 90 and a distal portion of a femur 100. More specifically, FIG. 1a is a sagittal illustration of a proximal end portion 92 of the tibia 90 and a distal end portion 102 of the femur 100, and FIG. 1b is a distal end illustration of the femur 100 and a sagittal plane 101. The tibia 90 has a mechanical axis 94 which extends from the center of the ankle to the center of the knee 80. Typically, the mechanical axis 94 of the tibia 90 is substantially vertical in the standard anatomical position, and may therefore alternatively be considered a superior-inferior axis 94. The distal end portion 102 of the femur 100 includes an epiphyseal region or distal femur 110 and a diaphyseal region or femoral shaft 120. The femur 100 may also include one or more landmarks 109 which indicate a boundary between the epiphyseal region 110 and the diaphyseal region 120.

The distal femur 110 includes a medial condyle 111, a lateral condyle 112, and an intercondylar region or trochlea 113, which includes a trochlear groove 114 and a trochlear notch 116. The trochlear groove 114 has a distalmost point 115, which may be utilized as a landmark in determining certain axes of the femur 100. The distal femur 110 also includes a transepicondylar axis (TEA) 117, a posterior condylar axis (PCA) 118, and a centroid 119. The centroid 119 may, for example, be the geometric center of the entire distal end portion 102, or the geometric center of only the distal femur 110.

The femoral shaft 120 includes compact bone 121 which surrounds a medullary canal 122. An anatomic axis 124 of the femur 100 extends along femoral shaft 120, and more particularly along the medullary canal 122. The anatomic axis 124 can be determined based on anatomical landmarks of the femur 100, such as the distalmost point 115 of the trochlear groove 114 and a center point 125 of the medullary canal 122 in a cross-section taken perpendicular to the shaft 120.

As noted above, the tibia 90 has a mechanical axis 94, which may be considered to define a superior-inferior axis 94 for the knee 80. Additionally, the anatomic axis 124 of the femur 100 intersects the superior-inferior axis 94 at the transepicondylar axis 117, and a flexion angle θ100 is defined between the superior-inferior axis 94 and the anatomic axis 124 on the sagittal plane 101. Flexion of the knee 80 causes relative pivoting of superior-inferior axis 94 and the anatomic axis 124 about the transepicondylar axis 117, thereby altering the flexion angle θ100. From a perspective which takes into account the entire anatomy of the patient, such flexion causes the tibia 90 to rotate about the transepicondylar axis 117 while the femur 100 remains generally stationary. However, from a perspective focused primarily on the knee 80, such flexion may equivalently be considered as causing the femur 100 to rotate about the transepicondylar axis 117 while the tibia 90 and the superior-inferior axis 94 remain stationary.

The knee 80 has a neutral flexion angle, which is defined as the flexion angle θ100 when the knee 80 is in a neutral extended position. In a typical healthy knee 80, the neutral flexion angle may be between zero degrees (0°) and two degrees (2°). In patients for whom a knee arthroplasty is medically indicated, however, the pre-operative neutral flexion angle may lie within another range, such as between two degrees (2°) and ten degrees (10°). For such patients, it may be desirable to manipulate the tibia 90 and/or the femur 100 to reduce the neutral flexion angle from the pre-operative neutral flexion angle to a target neutral flexion angle, such as one falling within the typical range for healthy knees. As described in further detail below, this may involve determining a flexion correction angle to be applied to the knee 80 during a surgical procedure to provide the knee 80 with the target neutral flexion angle.

Figure 2:
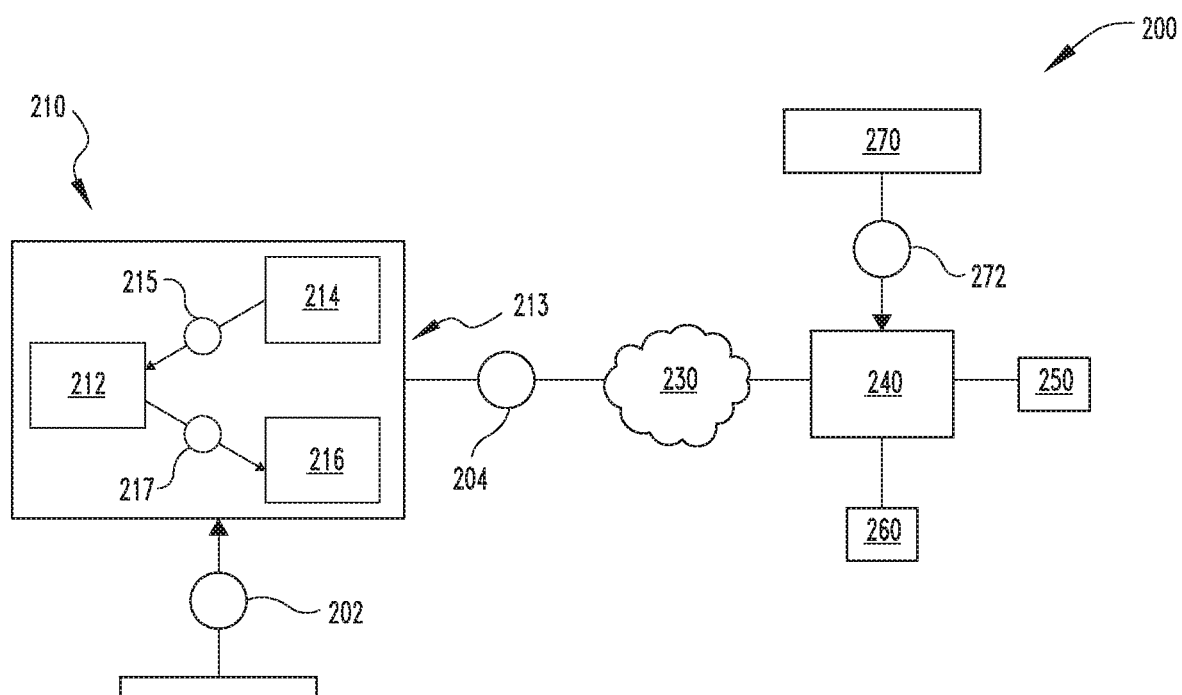
FIG. 2 is a schematic block diagram of a system according to certain embodiments.

FIG. 2 illustrates a system 200 according to one embodiment. The system 200 includes a design device 210, a design tool 220 in communication with the design device 210, a network 230 in communication with the design device 210, a server 240 in communication with the network 230, modeling tools 250 accessible by the server 240, a memory 260, and an imaging device 270 in communication with the server 240. An example of a computing device 500 which may be utilized in connection with one or more of the elements of the system 200 is described below with reference to FIG. 11. Although various elements of the system 200 are illustrated in FIG. 2 as discrete but connected elements, it is to be understood that one or more of the elements may be combined with another element or distributed among a plurality of the other elements. For example, while the memory 260 is illustrated as being in communication with the server 240, it is also contemplated that the memory 260 may be provided at the design device 210 and/or distributed across the network 230. Additionally, unless specified to the contrary, one or more of the illustrated elements may be omitted, and one or more elements that are not specifically illustrated in FIG. 2 may be included in the system 200.

The design device 210 is accessible by a user, such as a surgeon or a surgical planner, to enable the user to interact with the design device 210 and to enable the system 200 to perform one or more of the actions and operations described hereinafter. As examples, the design device 210 may be provided as a desktop computer, a laptop computer, a personal data assistant (PDA), a mobile handheld device, or a dedicated device. The design device 210 includes a processor 212, and may further include a user interface 213 including an input device 214 and/or a display device 216. The input device 214 may be any form of input operable to convert actions by a user into signals representative of input information 215. By way of example, the input device 214 may include one or more of a keyboard, a keypad, a touchpad, a mouse, a touchscreen, a camera, and/or a motion detector. Similarly, the display device 216 may be any form of display operable to convert output information 217 received from the processor 212 into a form identifiable to the user. By way of example, the display device 216 may include one or more of a monitor, a projector, a video screen, and/or a tactile interface. In certain embodiments, the user interface 213 may combine the input device 214 and the display device 216 in a single integral unit, such as a touchscreen. In certain embodiments, the user interface 213 may include plural input devices 214 and/or plural display devices 216, which may be located at separate locations.

The design tool 220 is accessible by the design device 210 to enable the tool 220 to provide patient information 202 to the design device 210. The tool 220 may be provided at the design device 210, or may be provided elsewhere, such as at the server 240. The patient information 202 may include diagnostic data, such as a digital X-ray image, a magnetic resonance image (MRI), or a computer tomography (CT) image. In certain embodiments, the information 202 may be representative of a model of at least a portion of the patient's anatomy. In certain embodiments, the tool 220 may enable the user to select certain points or elements associated with the information, such as points on the model. The tool 220 may enable the user to manipulate the image shown on the display device 216. For example, the system 200 may be configured to display the model on the display device 216, and the tool 220 may enable the user to zoom, translate, and/or rotate the model. In certain embodiments, the user interface 213 may include the tool 220, and/or the tool 220 may include one or both of the input device 214 and the display device 216.

The server 240 may, for example, be embodied as a computer. The server 240 may be enabled to receive and transmit information 204 between the surgeon's design device 210 and other elements of the system 200. Transmission of the information 204 may be performed over the network 230, which may be embodied as the Internet or as an intranet. The server 240 may be provided with modeling tools 250 which generate certain responses to information 204 received from the design device 210. In some embodiments, the tools 250 may include computer aided design (CAD) systems. Common CAD systems known in the art include SolidWorks® (produced by SolidWorks Corporation, 300 Baker Avenue, Concord, Mass. 01742) and Pro Engineer® (produced by Parametric Technology Corporation, 140 Kendrick Street, Needham, Mass. 02494). The CAD systems may be enabled to translate information 204 received from the design device 210 into a model or a modified model. For example, the CAD systems may generate an initial model based upon the patient information 202, and generate modifications of the model based upon the input information 215.

The imaging device 270 may for example, be embodied as an X-ray imaging device, an MRI imaging device, a CT imaging device, or another form of imaging device which generates imaging information 272 representative of a portion of a patient's anatomy. By way of example, the imaging information 272 may be digital data relating to images generated by the imaging device 270. In certain embodiments, the imaging information 272 may be provided to the design tool 220, and the design tool 220 may provide the imaging information 272 to the design device 210 as the patient information 202. In certain embodiments, the modeling tools 250 may generate a three-dimensional bone model based upon the imaging information 272, and the design tool 220 may provide the bone model to the design device 210 as the patient information 202. As described in further detail below, the imaging information 272 may represent the patient's anatomy with varying degrees of fidelity. For example, the imaging information 272 may include a higher-fidelity region which represents a corresponding portion of the anatomy with a higher degree of fidelity and a lower-fidelity region which represents a corresponding portion of the anatomy with a lower degree of fidelity. In such forms, a model based upon the imaging information may have higher-fidelity and lower-fidelity portions corresponding to the higher-fidelity and lower-fidelity regions of the imaging information 272.

Figure 3A:
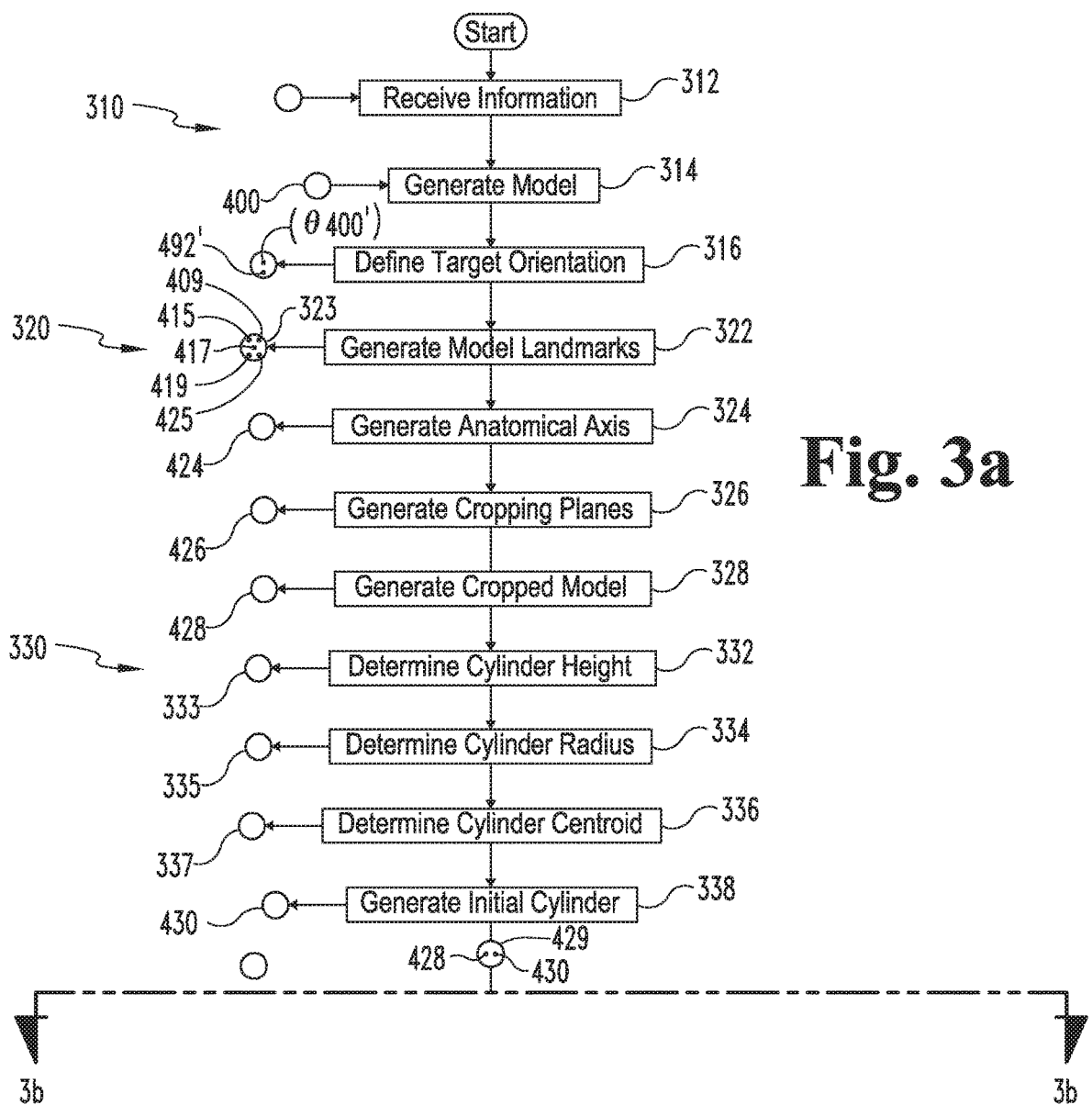
FIGS. 3a and 3b are a schematic flow diagram illustrating a process according to certain embodiments.
Figure 3B:
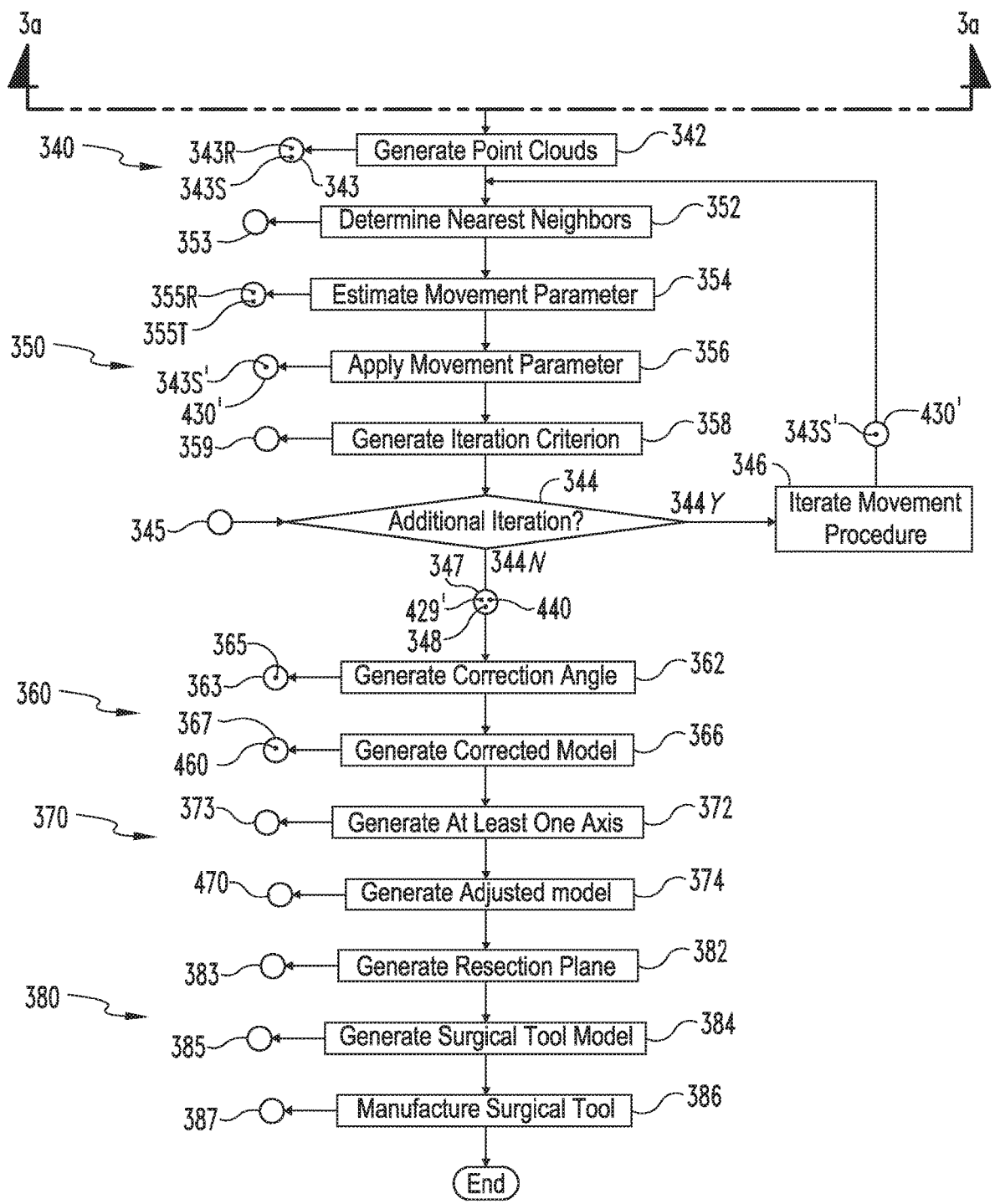

With additional reference to FIGS. 3-10, further details regarding a process according to certain embodiments will now be provided. FIG. 3 illustrates a process 300 that involves determining a correction angle 363 relating to a model of a long bone of a particular patient, and FIGS. 4-10 illustrate exemplary stages of the process 300. In the embodiment illustrated in the Figures and described hereinafter, the process 300 involves determining the correction angle 363 for a model 400 of at least a portion of a femur 100. As described in further detail below, however, it is also contemplated that the process 300 may be utilized to determine another form of correction angle, such as a correction angle for a model of another form of long bone.

Additionally, operations illustrated for the processes in the present application are understood to be examples only, and operations may be combined or divided, and added or removed, as well as re-ordered in whole or in part, unless explicitly stated to the contrary. Unless specified to the contrary, it is contemplated that certain operations, procedures, or steps performed in the process 300 may be performed wholly by the design device 210, the design tool 220, the network 230, the server 240, the modeling tools 250, or the imaging device 270, or that the operations or steps may be distributed among one or more of the elements of the system 200 and/or additional devices or systems which are not specifically illustrated in FIG. 2.

Generally speaking, the process 300 includes a modeling procedure 310, a cropping procedure 320, a cylinder generating procedure 330, a registering procedure 340, and a correction procedure 360, and may further include an adjustment procedure 370 and a surgical device procedure 380. As described in further detail below, the modeling procedure 310 generally involves generating a model 400 of at least a portion of a femur 100, and the cropping procedure 320 involves cropping the model 400 to generate a cropped model 428. Additionally, the cylinder generating procedure 330 involves generating an initial cylinder 430 based upon the cropped model 428, and the registering procedure 340 involves registering the cylinder 430 to the cropped model 428 to generate a registered cylinder 440. The correction procedure 360 involves generating a corrected model 460 based upon information generated during the registering procedure 340, and the adjustment procedure 370 involves generating an adjusted model 470 based upon the corrected model 460. The surgical device procedure 380 involves generating a surgical device model 385 based at least in part upon the adjusted model 470, and may further include manufacturing a surgical device 387 according to the model 385.

The modeling procedure 310 may begin with an operation 312, which includes receiving information 313 relating to a long bone of a particular patient, such as a femur 100. For example, the information 313 may include patient information 202 provided by the design tool 220, and the operation 312 may include receiving the patient information 202 at the design device 210. In certain embodiments, the received information 313 may include diagnostic imaging data 272 such as a digital X-ray image, an MRI, or a CT image generated by the imaging device 270. In other embodiments, the received information 313 may be information relating to or defining a model of the femur 100, such as a CAD model. By way of example, the patient information 202 may include model data defining the model 400, and the model data may be generated by the modeling tools 250 using the imaging information 272.

The modeling procedure 310 may continue to an operation 314, which includes generating a three-dimensional model 400 (e.g., a CAD model) of at least a portion of the femur 100 based upon the received information 313. In embodiments in which the received information 313 relates to the model 400, the operation 314 may involve generating the model 400 according to the model data of the received information 313. In embodiments in which the received information 313 relates to diagnostic imaging data, the operation 314 may include generating the model 400 based upon the imaging information 272. Generating the model 400 based upon the imaging information 272 may include segmenting or otherwise processing the imaging data to reconstruct the geometry and shape, or otherwise define the relevant surfaces and other morphological aspects of the femur 100. For example, individual image slices of MRI data may be processed to identify boundaries between the femur 100 and the surrounding anatomy and/or boundaries between the compact bone 121 and the medullary canal 122. Such segmenting may be accomplished by manual, automated, or semi-automated processes. In some embodiments, segmentation may be facilitated by software packages available from, for instance, Able Software Corp of Lexington, Mass. (3D-DOCTOR™), Materialise of Leuven, Belgium (MIMICS®) or other software, which may be included in the modeling tools 250. In some embodiments, other techniques may be used to process the imaging data 272, such as threshold based image processing, probabilistic atlas based, statistical shape modeling based, or other techniques. Some embodiments may at least partially utilize MATLAB® based processes (of MathWorks, Inc., Natick, Mass.) as part of such techniques.

Figure 4:
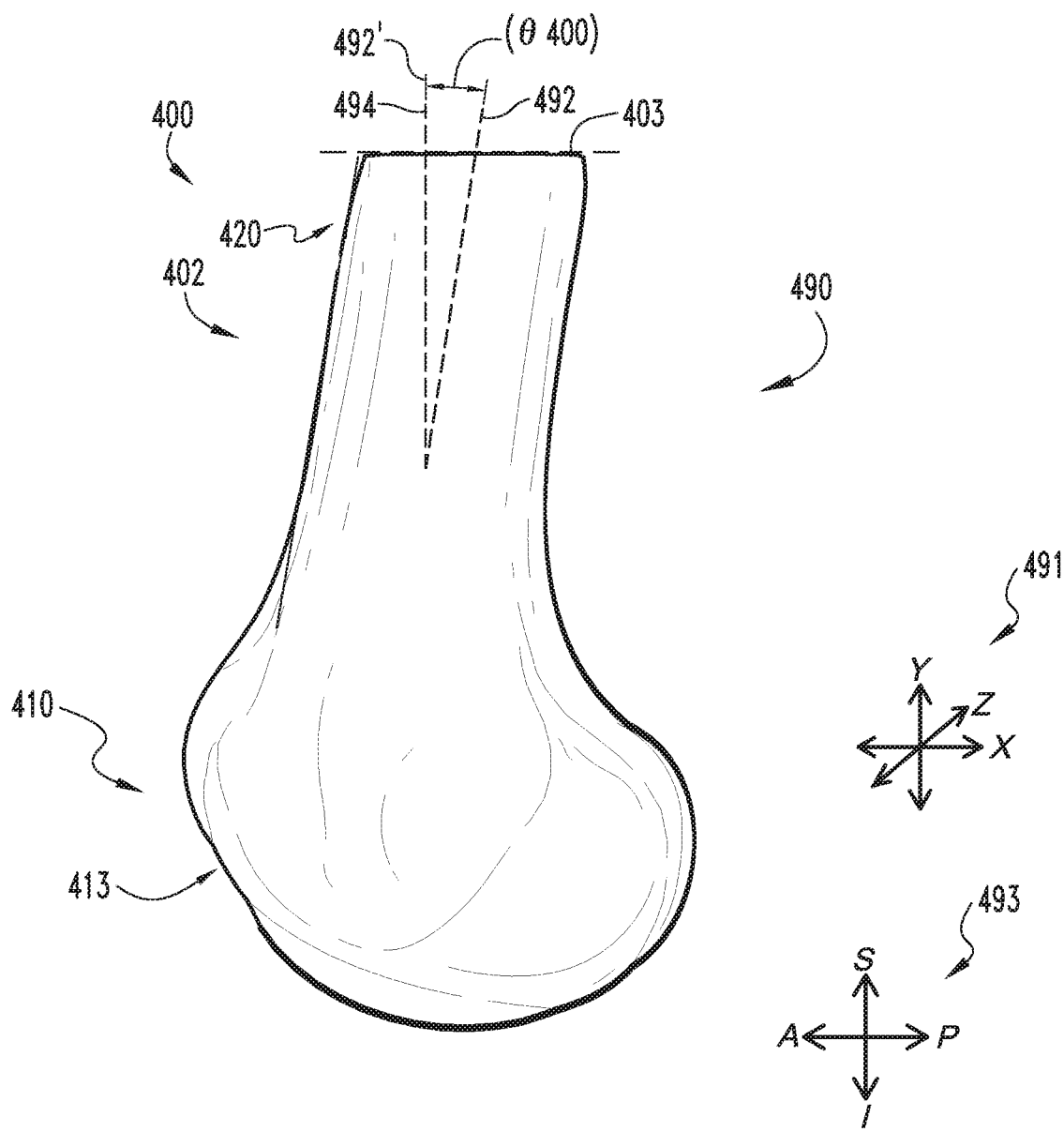
FIG. 4 is a sagittal illustration of a model of a distal end portion of a femur.

As illustrated in FIG. 4, the model 400 may be defined in a virtual three-dimensional space 490 having an associated coordinate system 491. The coordinate system 491 may include three mutually orthogonal axes, which may be defined by the imaging information 272 on which the model 400 is based. For example, when the received information 313 includes MRI data, two of the axes may correspond to the vertical and horizontal directions in each MM slice, and the third axis may be orthogonal to the planes of the slices.

The model 400 of at least a portion of the femur 100 includes a distal end portion model 402 representative of the femur distal end portion 102. In certain embodiments, the distal end portion model 402 may be a surface model representative of the outer surface of the femur distal end portion 102. The distal end portion model 402 may further include an inner surface representative of the boundary between the compact bone 121 and the medullary canal 122. The distal end portion model 402 includes a distal femur model 410 representative of the distal femur 110, and a femoral shaft model 420 representative of the femoral shaft 120. The proximal end of the distal end portion model 402 may define a proximal end plane 403. In certain embodiments, the operation 314 may include cropping the femur model 400 at a transverse plane, such that the proximal end plane 403 is defined as a transverse plane. In certain embodiments, the proximal end plane 403 may represent a boundary of the imaging data 272 used to generate the model 402. For example, when the model 402 is generated from MM data, the proximal end plane 403 may correspond to the location at which the MRI is cut off.

Whether the received information 313 relates to diagnostic imaging data or to the model 400 itself, the information 313 may include orientation information specifying the orientation of the femur 100 in the patient's current (i.e., pre-operative) neutral flexion angle. For example, the imaging information 272 may be generated with the knee 80 in a fully-extended position, and/or the received model data may be based upon such imaging information 272. Thus, the generated model 400 may include not only information relating to the structural features of the femur 100, but also information relating to the orientation of the femur 100 with respect to the patient's anatomy. For example, FIG. 4 illustrates the model 402 in an orientation corresponding to the patient's pre-operative flexion angle. More specifically, a central axis 492 of the femoral shaft model 420 is angularly offset from a superior-inferior axis 494 by a pre-operative neutral flexion angle θ400 defined along the sagittal plane.

When the model 400 is generated based upon diagnostic imaging data such as the imaging information 272, the orientation of the model 400 within the three-dimensional space 490 may depend not only on the patient's pre-operative neutral flexion angle θ400, but also upon the patient's position and orientation at the time of the imaging. If the femur 100 is not aligned with the axes of the imaging device 270, a model 400 generated from such imaging data may be improperly aligned within the three-dimensional space 490. For example, while the axes of the anatomical coordinate system 493 illustrated in FIG. 4 are parallel to the axes of the model coordinate system 491, the anatomical coordinate system 493 may be misaligned with the model coordinate system 491 if the femur 100 is not in an optimal position at the time of imaging.

The modeling procedure 310 may also include an operation 316, which includes defining a target orientation 317 for the model 400. In certain embodiments, the target orientation 317 may be based upon empirical data, the patient-specific information 202, and/or surgeon preference. In certain forms, the target orientation 317 may relate to a target neutral flexion angle θ400' for the femur 100 (e.g., a target value for the angle formed on the sagittal plane between the femoral shaft axis 124 and the superior-inferior axis 94). For example, the target orientation 317 may define the target neutral flexion angle θ400' as an angle between zero degrees (0°) and two degrees (2°). In certain forms, the target orientation 317 may include a vector 492' representative of a target orientation for the femoral shaft axis 492. For example, the vector 492' may be parallel to the superior-inferior axis 494 in the sagittal plane, or may be offset from the superior-inferior axis 494 in the sagittal plane by a predetermined angle, such as an angle between zero degrees (0°) and two degrees (2°).

As will be appreciated, two vectors need not lie on a common reference plane in order to calculate the angle between the vectors along the reference plane. For example, if the first vector lies on the reference plane and the second vector does not lie on the reference plane, the angle between the vectors along the reference plane may be obtained by determining the projection of the second vector onto the reference plane, and determining the angle between the first vector and the projection of the second vector. For example, if the target vector 492' does not lie on the sagittal plane, the sagittal plane angle between the superior-inferior axis 494 and the target vector 492' may be obtained by determining the angle between the superior-inferior axis 494 and the projection of the target vector 492' onto the sagittal plane. Similarly, if neither vector lies on the reference plane, the angle between the vectors along the reference plane may be determined by calculating the angle between the projections of the vectors onto the reference plane. The projection of a vector onto a reference plane may be determined, for example, by calculating the component of the vector that is orthogonal to the reference plane, and subtracting or otherwise removing the orthogonal component from the vector.

As noted above, the efficacy of certain pre-operative planning techniques may be affected by the orientation of the model 400 within the three-dimensional space 490. For example, if one or more steps of a particular technique are based upon the assumption that the femoral shaft model 420 is substantially vertical in the three-dimensional space 490, the accuracy of the technique may be undermined when the model 400 is improperly aligned. Accordingly, the target orientation 317 may be based upon the coordinate system 491 of the three-dimensional space 490 in which the model 400 is defined. For example, the target vector 492' may be parallel to one of the axes of the coordinate system 491.

Figure 5:
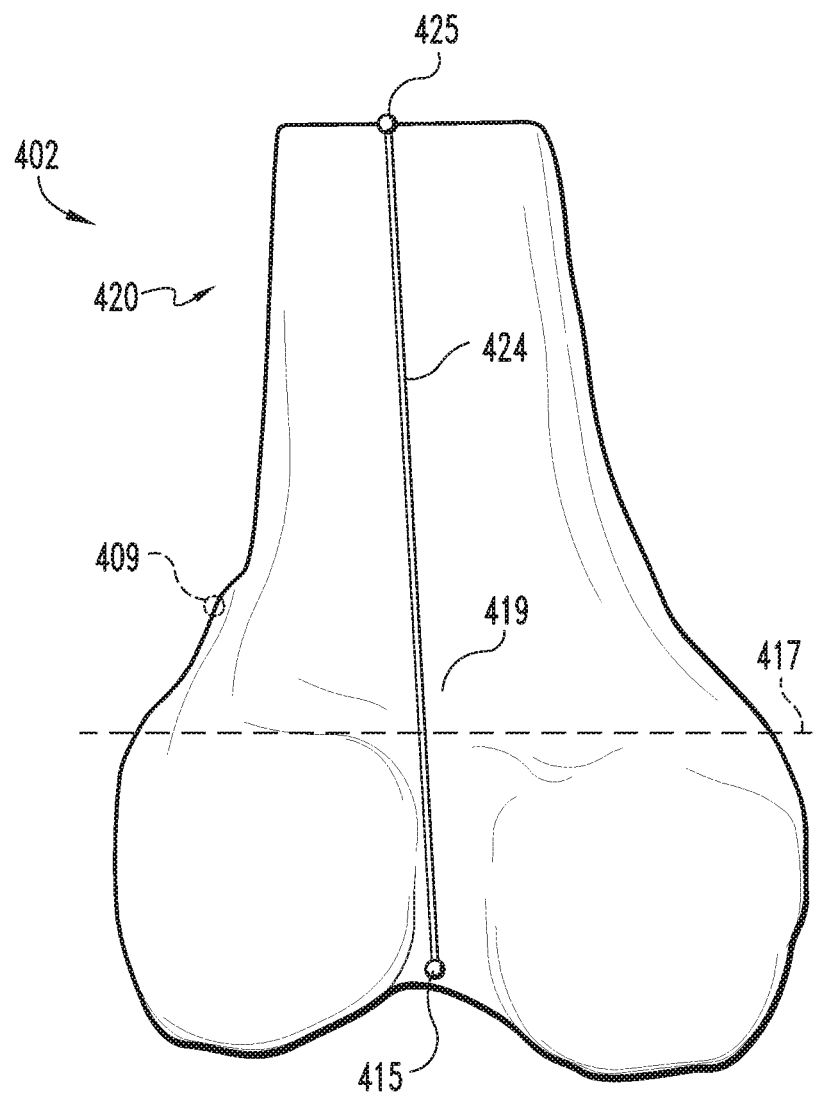
FIG. 5 is a coronal illustration of the model illustrated in FIG. 4.

With the distal end portion model 402 generated, the process 300 may continue to the cropping procedure 320. The cropping procedure 320 may begin with an operation 322, which includes generating a plurality of model landmarks 323 corresponding to anatomical landmarks of the femur 100. The model landmarks 323 may, for example, include the distalmost point 115 of the trochlear groove 114 and the center point 125 of the medullary canal 122. For example, FIG. 5 illustrates a distal landmark 415 corresponding to the distalmost point 115 of the trochlear groove 114, and a proximal landmark 425 corresponding to the center point 125 of the medullary canal 122. The model landmarks 323 generated during the operation 322 may also include one or more boundary landmarks 409 relating to a boundary between the distal femur model 410 and the femoral shaft model 420, a centroid landmark 419 corresponding to the geometric center of the distal end portion model 402, and/or additional or alternative landmarks not specifically illustrated in the Figures. For example, the operation 322 may include generating model landmarks 323 corresponding to the transepicondylar axis 417 of the distal femur model 410.

As will be appreciated, the model landmarks 323 may be generated by identifying points on the model 400 corresponding to the anatomical landmarks on the femur 100 using manual and/or automated techniques. In certain embodiments, the operation 322 may include identifying and generating one or more of the model landmarks 323 using techniques which are known to those having skill in the art and which need not be described in further detail herein. Additionally or alternatively, the operation 322 may include identifying and generating one or more of the model landmarks 323 using one or more of the techniques described hereinafter.

In certain embodiments, generating the proximal landmark 425 may include determining the center point of the distal end portion model 402 at the proximal end plane 403. For example, when the distal end portion model 402 is a surface model representative of the exterior surface of the distal end portion 102, the operation 322 may include generating the proximal landmark 425 at the central point of the outer perimeter of the model 402 at the proximal end plane 403. Alternatively, when the distal end portion model 402 includes a surface representative of the inner perimeter of the compact bone 121, the operation 322 may include generating the proximal landmark 425 at the central point of the inner perimeter of the model 402 at the proximal end plane 403.

In certain embodiments, the operation 322 may include generating the proximal landmark 425 by calculating the center point of the distal end portion model 402 near the proximal end plane 403. The proximal end plane 403 of the distal end portion model 402 may be defined as a transverse plane in the manner described above, or may alternatively be angularly offset from a transverse anatomical plane, for example if the femur 100 is not fully aligned with the imaging axes of the imaging device 270. In the latter case, the cross-section of the femoral shaft model 420 at the proximal end plane 403 may exhibit distortion, thereby leading to an inaccurate calculation of the center point of the femoral shaft 120. To correct for this distortion, the operation 322 may include generating a plane perpendicular to the femoral shaft model 420, and calculating the center point of the distal end portion model 402 at the plane. The perpendicular plane may, for example, be generated as the plane in which the outer perimeter or inner perimeter of the distal end portion model 402 is minimized.

With the model landmarks 323 generated, the procedure 320 may continue to an operation 324. The operation 324 includes generating an anatomic axis vector 424 representative of the anatomic axis 124 of the femur 100. The operation 324 may include generating the anatomic axis vector 424 as a line extending between the distal landmark 415 and the proximal landmark 425. In the illustrated form, the distal landmark 415 and the proximal landmark 425 respectively correspond to the distalmost point 115 of the trochlear groove 114 and the center point 125 of the medullary canal 122. It is also contemplated that additional or alternative landmarks may be utilized, and that the operation 322 may involve generating model landmarks 323 corresponding to the additional or alternative anatomical landmarks of the femur 100. Such anatomical landmarks may, for example, include one or more of a lateral peak, a medial peak, a lateral distal point, a medial distal point, a lateral epicondyle, a medial epicondyle, and/or an adductor tubercle.

Figure 6:
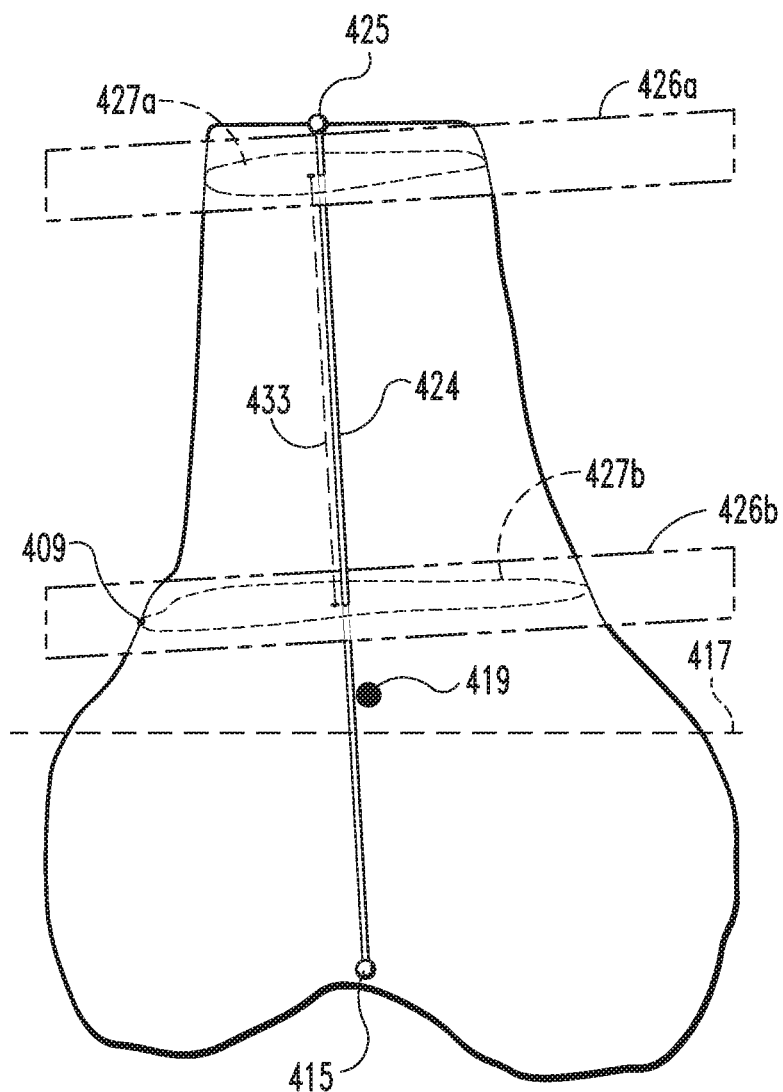
FIG. 6 illustrates the model of FIG. 5 and generated cropping planes.

With the anatomic axis vector 424 generated, the procedure 320 may continue to an operation 326. In the illustrated form, the operation 326 includes generating a pair of cropping planes 426 based at least in part upon the anatomic axis vector 424, for example as illustrated in FIG. 6. As described in further detail below, the operation 326 includes generating a proximal cropping plane 426a and a distal cropping plane 426b, one or both of which may be orthogonal to the anatomic axis vector 424. The procedure 320 may then continue to an operation 328, which includes generating a cropped model 428 (FIG. 7) based on the cropping planes 426 and the distal end portion model 402. For example, the operation 328 may include cropping the distal end portion model 402 such that the cropped model 428 includes only the portion of the distal end portion model 402 that is located between the cropping planes 426.

As will be appreciated, the fidelity of certain imaging techniques may vary according to a number of factors. In MIII scans, for example, geometric distortion and MIII coil cutoff may result in a certain portion of the diaphyseal region 120 being represented with less fidelity than other regions. In a model 400 generated from such an MM scan, it may be the case that certain regions of the femoral shaft model 420 may represent the femoral shaft 120 less accurately than other regions of the femoral shaft model 420. In certain embodiments, the cropping planes 426 may be generated such that the lower-fidelity portions of the distal end portion model 402 are removed in the operation 328. In other words, the cropped model 428 may include the portion of the distal end portion model 402 which represents the femoral shaft 120 with a threshold level of fidelity.

The proximal plane 426a is located near the proximal end of the femoral shaft model 420, and an intersection 427a of the proximal plane 426a and the distal end portion model 402 defines a proximal boundary for the cropped model 428. The proximal plane 426a may be generated such that the intersection 427a has a continuous outer perimeter. In certain embodiments, the proximal plane 426a may be the proximal-most plane for which the intersection 427a has a continuous outer perimeter. In other embodiments, the operation 326 may include generating the proximal plane 426a at least a predetermined distance from the distal end plane 403. In certain embodiments, the operation 326 may include generating the proximal plane 426a at the proximal landmark 425, for example in embodiments in which generating the proximal landmark 425 includes generating a plane perpendicular to the femoral shaft model 420.

As noted above, one factor that may adversely affect the fidelity of diagnostic imaging information 272, and therefore the fidelity of a model 402 generated from such imaging data, is MRI coil cutoff. For example, if the distal end portion model 402 is generated from MRI data, the region near the proximal end plane 403 may have a lower fidelity than a more distal region of the model 402. In certain embodiments, the operation 326 may include generating the proximal plane 426a such that the lower-fidelity regions are removed in the operation 328. For example, the operation 326 may include generating the proximal plane 426a a predetermined distance from the proximal landmark 425.

The distal plane 426b is located near the distal end of the femoral shaft model 420, and an intersection 427b of the distal plane 426b and the distal end portion model 402 defines a distal boundary of the cropped model 428. In certain embodiments, the operation 326 may include defining the distal plane 426b such that the cropped model 428 is generally cylindrical. While the femoral shaft model 420 may be generally cylindrical, the proximal end of the distal femur model 410 may include a flared portion corresponding to the metaphysis of the femur 100. In certain embodiments, the operation 326 may include generating the distal plane 426b at or near the boundary between the distal femur model 410 and the femoral shaft model 420, for example by using the one or more boundary landmarks 409. In certain embodiments, the operation 326 may include generating the distal plane 426b a predetermined distance from distal landmark 415, or a predetermined distance from the centroid landmark 419.

As noted above, the cropping planes 426 may be generated such that the cropped model 428 is generally cylindrical and represents a portion of the femoral shaft 120 with a desired degree of fidelity. In certain embodiments, the operation 326 may include generating one or both of the cropping planes 426 based upon one or more criteria relating to the correlation of the cropped model 428 to a cylinder. Such criteria may relate to a ratio between the cross-sectional areas of the proximal and distal intersections 427a, 427b. By way of example, the operation 326 may include generating the proximal plane 426a a predetermined distance from the proximal landmark 425, determining the cross-sectional area of the proximal intersection 427a, and generating the distal plane 426b at a location at which the cross-sectional area of the distal intersection 427b is related to the cross-sectional area of the proximal intersection by the ratio.

In certain embodiments, the operation 326 may include generating one or both of the cropping planes 426 based upon one or more of the model landmarks 323. As noted above, one or both of the cropping planes 426 may be generated at a predetermined distance from a corresponding one of the model landmarks 323. In certain embodiments, the predetermined distance may be generated based upon empirical data 327. As one example, the empirical data 327 may indicate that a particular diagnostic imaging technique lacks the desired fidelity within a given distance of the borders of the image, and the operation 326 may include generating the proximal plane 426a at least a corresponding distance from the proximal end plane 403. In certain forms, the operation 326 may include defining an offset region corresponding to the region in which the diagnostic imaging technique lacks the desired fidelity. For example, the operation 326 may include defining the offset region adjacent the proximal end plane 403 of the distal end portion model 402, and generating each of the cropping planes 426 outside of the offset region.

In certain embodiments, empirical data 327 may be provided for a number of different patient population sets (e.g., corresponding to gender, age, medical condition, femur size, etc.), and the operation 326 may include generating the cropping planes 426 based upon the set of empirical data 327 corresponding to the particular patient. For example, the empirical data 327 may indicate that the distal end of the diaphyseal region 120 is most likely to be located a given distance from the distalmost point 115, and the operation 326 may include generating the distal plane 426b at a corresponding distance from the distal landmark 415. As another example, the empirical data 327 may indicate that an anatomical landmark 109 corresponds to the proximal end of the epiphyseal region 110, and the operation 326 may include generating the distal plane 426b at the boundary landmark 409 corresponding to the anatomical landmark 109.

With the cropped model 428 generated, the process 300 may continue to the cylinder generating procedure 330, which generally involves generating a cylinder 430 corresponding to the cropped model 428. More specifically, the procedure 330 includes determining a plurality of parameters for the cylinder 430, and generating the cylinder 430 based upon the parameters. As described in further detail below, the cylinder parameters may include one or more of a height 333, a radius 335, and a centroid 337. While the illustrated cylinder 430 is a circular cylinder, it is also contemplated that the cylinder 430 may take another form. For example, the cylinder 430 may be provided as an elliptical cylinder, the procedure 330 may further include determining additional or alternative cylinder parameters, such as a major radius, a minor radius, and/or an eccentricity.

The illustrated procedure 330 includes an operation 332, which includes determining a height 333 for the cylinder 430. The operation 332 may include determining the height 333 based upon the length 433 of the anatomic axis vector 424 between the cropping planes 426, for example as illustrated in FIG. 6. As will be appreciated, the height 333 is the dimension of the cylinder 430 along the longitudinal axis 431. In certain embodiments, the operation 332 may include determining an orientation for the longitudinal axis 431 based upon the target orientation 317. For example, when the target orientation 317 is defined based upon the coordinate system 491, the operation 332 may include defining the longitudinal axis orientation parallel to one of the axes of the coordinate system 491.

Figure 7:
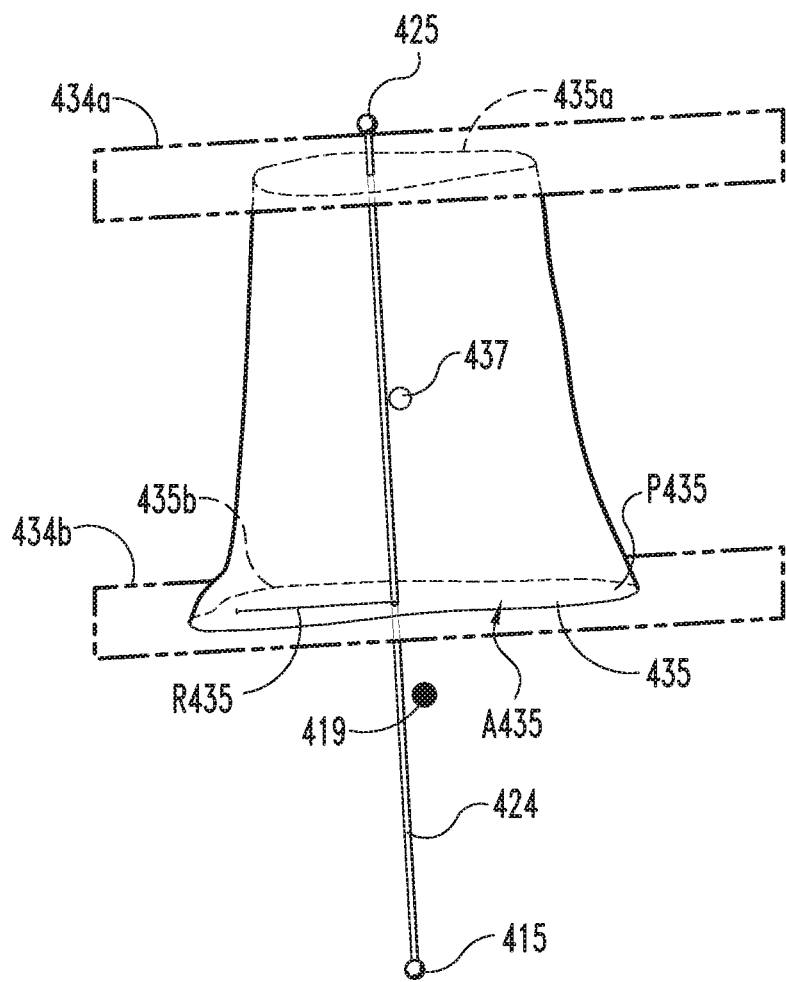
FIG. 7 is an illustration of a cropped model corresponding to a portion of the model illustrated in FIG. 6.
Figure 8:
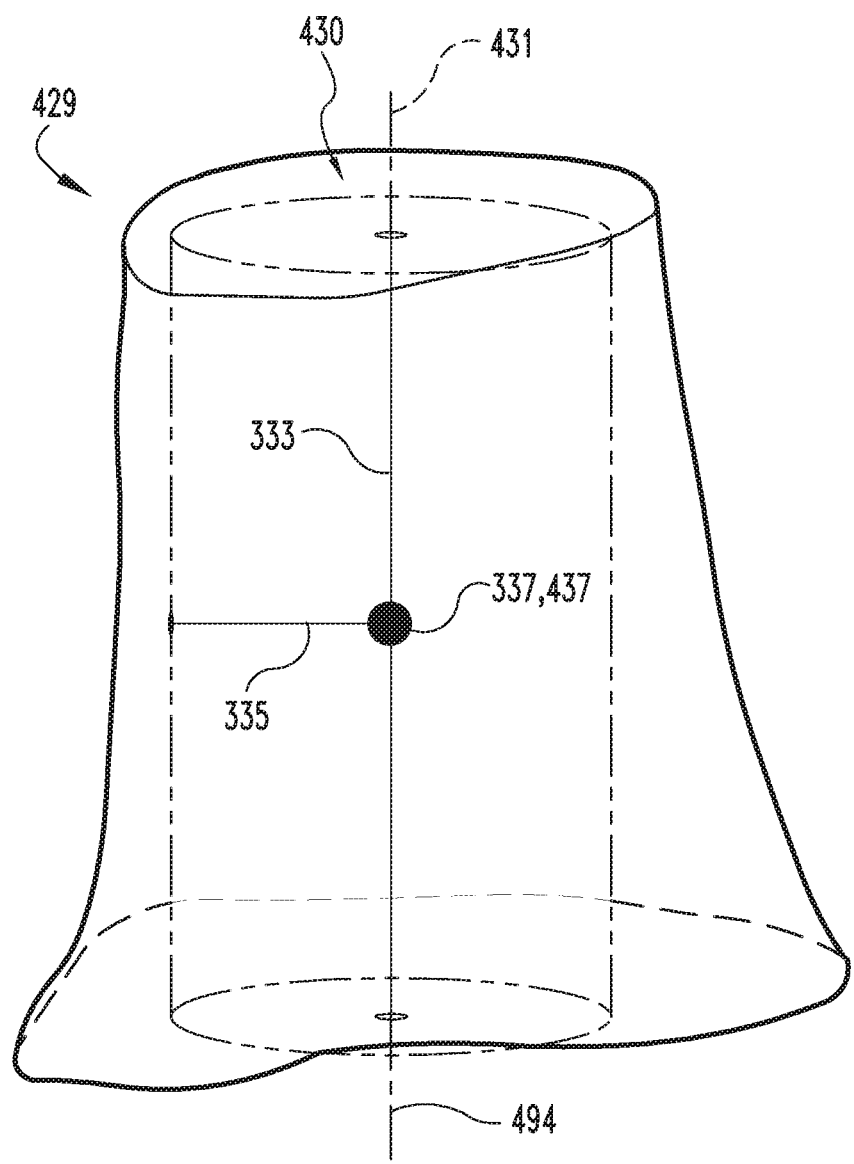
FIG. 8 illustrates a registration model including the cropped model and an initial cylinder.

The procedure 330 also includes an operation 334, which includes determining a radius 335 for the cylinder 430. The operation 334 may include determining the radius 335 based upon an average radius of the cropped model 428. By way of example, the operation 334 may include generating a plurality of planes 434 that are orthogonal to the anatomic axis vector 424, and which define intersections 435 with the cropped model 428, for example as illustrated in FIG. 7. While only two planes 434 are illustrated in FIG. 7, it is to be appreciated that the operation 334 may include generating additional planes 434, for example at constant intervals along the anatomic axis vector 424. The operation 334 may further include determining one or more geometric properties of each intersection 435, and determining an equivalent radius R435 for each intersection 435 based upon the geometric property. As one example, the geometric property may be an area A435 of the intersection 435, and the equivalent radius R435 may be calculated using the equation $R435=\sqrt{A435/\pi}$. As another example, the geometric property may be a perimeter P435 of the intersection 435, and the equivalent radius R435 may be calculated using the equation $R435=P435/(2\pi)$. The operation 334 may further include defining the cylinder radius 335 as the average of the equivalent radii R435 for the plurality of intersections 435.

The procedure 330 may also include an operation 336, which includes determining a centroid 337 for the cylinder 430. The operation 336 may include determining the centroid 337 for the cylinder 430 based upon the centroid 437 of the cropped model 428. The centroid 437 of the cropped model 428 may be the geometric center point of the cropped model 428, which may be determined using any of a number of known techniques. By way of example, the cropped model centroid 437 may be determined by generating a three-dimensional array of evenly spaced points, and calculating the mean position of the subset of points that fall within the cropped model 428.

With the cylinder parameters determined, the procedure 330 may continue to an operation 338, which includes generating the cylinder 430 based upon the parameters. In the illustrated form, the operation 338 includes generating the cylinder 430 having the determined height 333 and radius 335 such that the cylinder centroid 337 coincides with the cropped model centroid 437 and the longitudinal axis 431 of the cylinder 430 corresponds to the target orientation 317. For example, if the target orientation 317 includes a target neutral flexion angle θ400' of zero degrees (0°), the operation 338 may include generating the cylinder 430 such that the longitudinal axis 431 extends parallel to the superior-inferior axis 494. As another example, if the target orientation 317 includes the orientation vector 492', the operation 338 may include generating the cylinder 430 with the longitudinal axis 431 extending parallel to the vector 492'.

With the cylinder 430 generated, the cylinder 430 and the cropped model 428 may be considered to define a registration model 429, and the process 300 may continue to the registering procedure 340, which involves registering the cylinder 430 to the cropped model 428. In the registering procedure 340, the registration model 429 may be considered to include a reference model and a source model, wherein the reference model corresponds to one of the cropped model 428 and the cylinder 430, and the source model corresponds to the other of the cropped model 428 and the cylinder 430. As described in further detail below, the registering procedure 340 involves generating a registered model 429' based upon the registration model 429. More specifically, the procedure 340 involves generating a registered cylinder 440, which includes registering the cylinder 430 to the cropped model 428 by rotating and translating one of the models with reference to the other of the models.

In the illustrated form, the reference model is the cropped model 428, the source model is the cylinder 430, and the procedure 340 includes generating the registered model 429' by rotating and translating the source model (i.e., the cylinder 430) with respect to the reference model (i.e., the cropped model 428). In other embodiments, the cropped model 428 may define the source model, the cylinder 430 may define the reference model, and the procedure 340 may include generating the registered model 429' by rotating and translating the source model (i.e., the cylinder 430) with respect to the reference model (e.g., the cropped model 428).

In the illustrated form, the registering procedure 340 involves an iterative closest point (ICP) registration procedure. The procedure 340 may begin with an operation 342, which includes generating point clouds 343 for the cropped model 428 and the cylinder 430. More specifically, the operation 342 includes generating a reference point cloud 343R on the surface of the reference model (e.g., the cropped model 428) and generating a source point cloud 343S on the surface of the source model (e.g., the cylinder 430).

The registering procedure 340 also includes at least one iteration of a movement procedure 350. The movement procedure 350 may begin with an operation 352, which includes generating nearest neighbor information 353 based upon the point clouds 343. More specifically, the nearest neighbor information 353 associates each point in one of the point clouds 343 with a nearest neighbor point in the other of the point clouds 343. In the illustrated form, the operation 352 includes determining, for each point in the source point cloud 343S, which point in the reference point cloud 343R is nearest, and the nearest neighbor information 353 associates each point in the source point cloud 343S to the corresponding point in the reference point cloud 343R. In other embodiments, the operation 352 may include determining, for each point in the reference point cloud 343R, which point in the source point cloud 343S is nearest, and generating the nearest neighbor information 353 to associate each point in the reference point cloud 343R to the corresponding point in the source point cloud 343S.

The movement procedure 350 also includes an operation 354, which generally includes generating a movement parameter 355 based at least in part upon the nearest neighbor information 353. The operation 354 includes generating the movement parameter 355 as the combination of a rotation matrix 355R and a translation vector 355T which, when applied to the source model (e.g., the cylinder 430), will increase a statistical correlation between the source point cloud 343S and the reference point cloud 343R. As described in further detail below, the statistical correlation may relate to an average offset between each point in the source point cloud 343S and the corresponding point in the reference point cloud 343R, such as an average root-mean-square offset or a mean absolute distance. In certain embodiments, the operation 354 may include estimating an optimal value for the movement parameter 355, wherein the optimal value is the value of the movement parameter 355 which maximizes the correlation between each point in the source point cloud 343S and the nearest neighbor point in the reference point cloud 343R. By way of example, the operation 354 may include estimating the movement parameter 355 using a mean squared error cost function to best align the points associated with one another by the nearest neighbor information 353.

With the movement parameter 355 generated, the movement procedure 350 may continue to an operation 356, which includes applying the movement parameter 355 to the cylinder 430 (i.e., the source model) to generate an updated cylinder 430'. For example, the operation 356 may include translating the cylinder 430 according to the translation vector 355T and rotating the cylinder 430 according to the rotation matrix 355R. The operation 356 may further include generating an updated source point cloud 343S' by applying the movement parameter 355 to the source point cloud 343S such that the updated source point cloud 343S' remains aligned with the updated cylinder 430'. In certain forms, the source point cloud 343S may be mapped to the source model (e.g., the cylinder 430) such that the source model may be considered to include the source point cloud 343S. In such forms, the updated source point cloud 343S' and the updated source model (e.g., the updated cylinder 430') may be contemporaneously generated as a result of applying the movement parameter 355 to the source model (e.g., the cylinder 430).

The movement procedure 350 may further include an operation 358, which includes generating an iteration criterion 359 relating to at least one feature of the current iteration of the movement procedure 350. In certain embodiments, the iteration criterion 359 may relate to a feature of the updated cylinder 430'. As one example, the iteration criterion 359 may relate to the orientation of the updated cylinder 430', such as an orientation of the longitudinal axis 431 in the sagittal plane, which may be obtained by projecting the longitudinal axis 431 onto the sagittal plane in the manner described above. As another example, the iteration criterion 359 may relate to the positions of the points in the updated source point cloud 343S'.

As another example, the iteration criterion 359 may relate to a statistical correlation between the updated source point cloud 343S' and the reference point cloud 343R. In certain embodiments, the statistical correlation may take the form of a root-mean-square average offset between each point in the updated source point cloud 343S' and the nearest neighbor point in the reference point cloud 343R. In other embodiments, the statistical correlation may take the form of a mean absolute distance between each point in the updated source point cloud 343S' and the nearest neighbor point in the reference point cloud 343R. In certain embodiments, the statistical correlation may correspond to the statistical correlation which is used to estimate the movement parameter 355 in the operation 354.

In certain embodiments, the iteration criterion 359 may relate to another feature of the current iteration of the movement procedure 350. As one example, the iteration criterion 359 may relate to the number of iterations of the movement procedure 350 that have been performed thus far in the registering procedure 340. As another example, the iteration criterion 359 may relate to the movement parameter 355 or a portion of the movement parameter 355, such as the rotation matrix 355R, the translation vector 355T.

With an iteration of the movement procedure 350 complete, the registering procedure 340 may continue to a conditional 344, which generally involves determining whether or not to perform an additional iteration of the movement procedure 350. The conditional 344 may include determining whether or not to perform the additional iteration based upon a comparison of the iteration criterion 359 and a comparison criterion 345. The conditional 344 may yield a negative first result 344N when the comparison indicates that an additional iteration of the movement procedure 350 need not be performed, and may yield a positive second result 344Y when the comparison indicates that an additional iteration of the movement procedure 350 is warranted. In certain embodiments, the conditional 344 may yield the negative result 344N when the iteration criterion 359 satisfies the comparison criterion 345. In other embodiments, the conditional 344 may yield the negative result 344N when the iteration criterion 359 violates the comparison criterion 345. In response to the negative result 344N, the process 300 may continue to the correction procedure 360. In response to the positive result 344Y, the process 300 may continue to an operation 346, which is described in further detail below.

In certain forms, the iteration criterion 359 may relate to the orientation of the longitudinal axis 431 of the updated cylinder 430'. In such forms, the comparison criterion 345 may relate to the target orientation 317 and a threshold correlation between the longitudinal axis 431 and the target orientation 317. The conditional 344 may yield the positive result 344Y when the difference between the orientation of the longitudinal axis 431 and the target orientation 317 exceeds the threshold of the comparison criterion 345, thereby indicating that another iteration is warranted. Conversely, the conditional 344 may yield the negative result 344N when the difference between the orientation of the longitudinal axis 431 and the target orientation 317 falls within the threshold of the comparison criterion 345, thereby indicating that the longitudinal axis 431 of the updated cylinder 430' is sufficiently close to the target orientation 317 and that the additional iteration of the movement procedure 350 is not warranted.

In certain forms, the iteration criterion 359 may include the correlation value, and the comparison criterion 345 may include a threshold value indicative of a sufficient correlation between the updated source point cloud 343S' and the reference point cloud 343R. In other words, the threshold value may indicate that the updated source point cloud 343S' matches the reference point cloud 343R with an acceptable accuracy. In such forms, the conditional 344 may yield the positive result 344Y when the correlation value of the iteration criterion 359 fails to meet the threshold value of the comparison criterion 345, thereby indicating that another iteration is warranted. Conversely, the conditional 344 may yield the negative result 344N when the correlation value of the iteration criterion 359 meets the threshold value of the comparison criterion 345, thereby indicating that the additional iteration of the movement procedure 350 is not warranted.

In certain forms, the comparison criterion 345 may include the iteration criterion 359 of a prior iteration of the movement procedure 350, and may further include a threshold value indicative of a sufficient correlation between the iteration criteria 359 of the current and prior iterations of the movement procedure 350. In such embodiments, the threshold value may indicate that the change in the iteration criterion 359 from the prior iteration to the current iteration is sufficiently small, thereby indicating that the process 300 has converged on a solution. For example, the iteration criterion 359 may be representative of the longitudinal axis 431, and the conditional 344 may include determining an angular and/or spatial offset between the longitudinal axis 431 of the current iteration and the longitudinal axis 431 of the prior iteration. An offset violating the threshold of the comparison criterion 345 may indicate that the process 300 has not yet converged sufficiently. The conditional 344 may accordingly yield the positive result 344Y, thereby indicating that an additional iteration is warranted. Conversely, an offset satisfying the threshold of the comparison criterion 345 may indicate that the process 300 has sufficiently converged on a solution, and that additional iterations are not warranted. The conditional 344 may accordingly yield the negative result 344N, thereby indicating that the additional iteration of the movement procedure 350 is not warranted.

In certain forms, the iteration criterion 359 may be representative of the number of iterations of the movement procedure 350 performed thus far in the registering procedure 340, and the comparison criterion 345 may include a threshold value for the number of iterations to be performed. In such embodiments, the conditional 344 may yield the positive result 344Y when the number of iterations indicated by the iteration criterion 359 falls below the threshold value of the comparison criterion 345, and may yield the negative result 344N when the number of iterations performed meets or exceeds the threshold value.

In certain forms, the iteration criterion 359 may relate to the movement parameter 355, and the comparison criterion 345 may include a threshold for the movement parameter 355. For example, a movement parameter 355 which falls below the threshold may indicate that the registering procedure 340 has sufficiently converged on a solution, and that the additional iteration of the movement procedure 350 is not warranted. In such embodiments, the conditional 344 may yield the positive result 344Y when the movement parameter 355 exceeds the threshold of the comparison criterion 345, and may yield the negative result 344N when the movement parameter 355 falls below the threshold.

In certain forms, the iteration criterion 359 and/or the comparison criterion 345 may include multiple criteria, and the conditional 344 may be based upon a comparison of the multiple criteria. For example, the iteration criterion 359 may include the correlation value and the number of iterations performed, and the comparison criterion 345 may include threshold values for the correlation value and the number of iterations performed. In this example, the conditional 344 may include comparing the correlation value and the number of iterations performed to the threshold values, and yielding the negative result 344N when either the correlation value or the number of iterations performed satisfies the corresponding threshold of the comparison criterion 345.

In certain forms, the conditional 344 may yield the negative result 344N when a predetermined number of the iteration criteria 359 satisfy the corresponding one of the comparison criteria 345. In certain forms, the conditional 344 may yield the positive result 344Y when a predetermined number of the iteration criteria 359 violate the corresponding one of the comparison criteria 345. Additionally, one or more of the comparison criteria 345 may be designated as a necessary criterion or a sufficient criterion, and the conditional 344 may include evaluating the necessity and/or sufficiency of one or more satisfied comparison criteria 345.

As noted above, the positive result 344Y of the conditional 344 indicates that an additional iteration of the movement procedure 350 is warranted. In response to the positive result 344Y, the registering procedure 340 may continue to an operation 346, which generally includes returning to the operation 352 and performing an additional iteration of the movement procedure 350. More specifically, the operation 346 includes performing the additional iteration of the movement procedure 350 using the updated source model (e.g., the updated cylinder 430') in place of the previously-generated source model (e.g., the initial cylinder 430 or the updated cylinder 430' of the prior iteration) and the updated source point cloud 343S' in place of the previously-generated source point cloud 343S.

As additional iterations of the movement procedure 350 are performed, the updated source models (e.g., the updated cylinders 430') may begin to converge, thereby indicating that the registering procedure 340 is approaching a final solution for the registered model 429'. As noted above, the registering procedure 340 may involve determining whether the iterations of the movement procedure 350 have converged on such a solution based upon the iteration criterion 359 and the comparison criterion 345, which may include the iteration criterion 359 of a previously-performed iteration of the movement procedure 350 and/or a threshold criterion. Additionally, the conditional 344 may include determining a delta value indicative of a change between the iteration criteria 359 of the current and previously-performed iterations, and comparing the delta value with the threshold criterion to determine whether or not the additional iteration of the movement procedure 350 is warranted. By way of example, the conditional 344 may include determining a delta value indicative of the difference in the correlation values (e.g., the values relating to the correlation between the updated source point cloud 343S' and the reference point cloud 343R) of the current and previous iterations, and determining that an additional iteration is warranted when the delta value exceeds the threshold. Further examples relating to determining the convergence of the iterations are provided above.

The process 300 also includes generating registration information 347 related to information generated during the registering procedure 340. In the illustrated form, the registration information 347 is generated in response to the negative result 344N of the conditional 344. In other embodiments, the registration information 347 may be generated at least in part during iterations of the movement procedure 350. As described in further detail below, the registration information 347 may include information relating to a total movement parameter 348, the registered model 429', and/or the registered cylinder 440.

In certain embodiments, the registration information 347 may include a total movement parameter 348 related to the total movement applied to the source model (e.g. the cylinder 430) during the successive iterations of the movement procedure 350. By way of example, the total movement parameter 348 may take the form of a total rotation matrix 348. In certain forms, the total rotation matrix 348 may be generated based upon a comparison of the longitudinal axes 431 of the initial cylinder 430 and the registered cylinder 440. In certain forms, the total rotation matrix 348 may be updated during each iteration of the movement procedure 350. For example, the first iteration of the movement procedure 350 may include storing the rotation matrix 355R as the total rotation matrix 348, and each subsequent iteration of the movement procedure 350 may include multiplying the current total rotation matrix by the current rotation matrix 355R to generate an updated total rotation matrix. In other embodiments, the total rotation matrix 348 may be obtained by multiplying all rotation matrices 355R in the order in which the rotation matrices 355R were generated.

Figure 9:
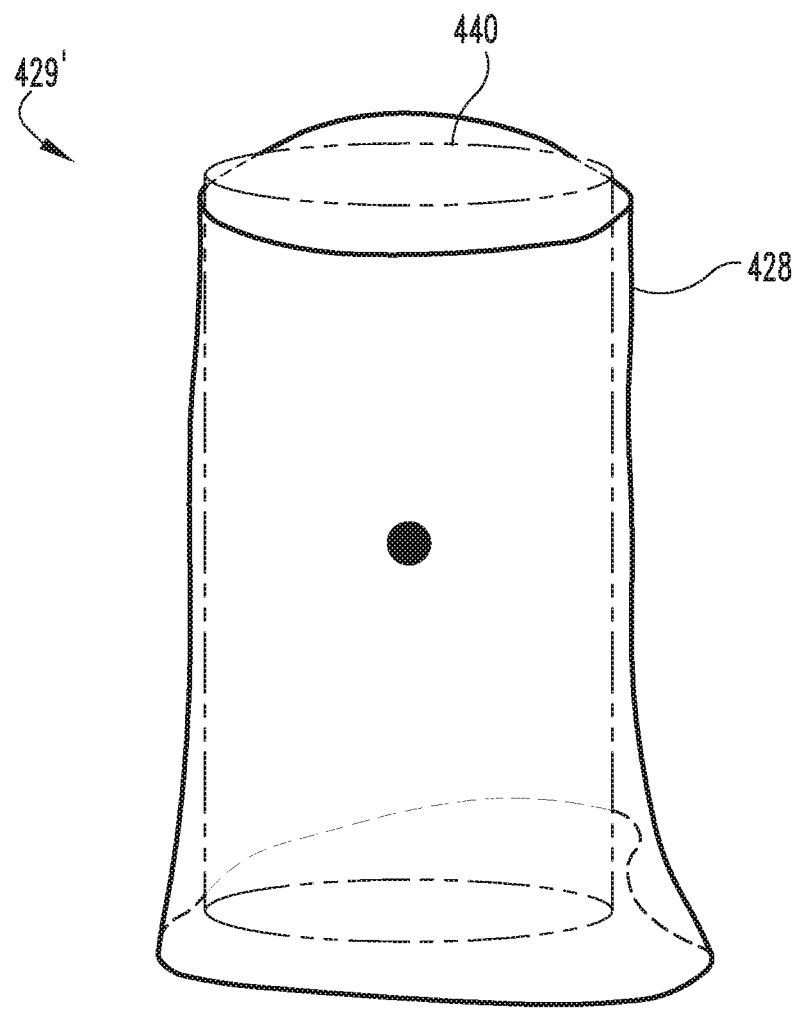
FIG. 9 illustrates a registered model including the cropped model and a registered cylinder.

In certain forms, the registration information 347 relates to a registered model 429', which may be generated based upon the original reference model (e.g., the cropped model 428) and the most recent iteration of the updated source model (e.g., the updated cylinder 430' of the most recent iteration of the movement procedure 350). For example, FIG. 9 illustrates a registered model 429' including the cropped model 428 and the registered cylinder 440. In the orientation illustrated in FIG. 9, the registered model 429' has been reoriented with respect to the orientation of the registration model 429 illustrated in FIG. 8 such that it appears that the cropped model 428 has been moved with respect to the cylinder 430/440. As will be appreciated, a similar orientation may result in embodiments in which the cylinder 430 is used as the reference model and the cropped model 428 is used as the source model.

While the registering procedure 340 has been described with reference to one embodiment of an iterative closest point procedure, it is to be understood that the cylinder 430 may be registered to the cropped model 428 using other techniques. In certain embodiments, the registering procedure 340 may include registering the cylinder 430 to the cropped model 428 using a variant of the described iterative closest point procedure, such as Sparse ICP (available from Computer Graphics and Geometry Laboratory, BC 347, Station 14, CH-1015 Lausanne, Switzerland) or an implementation of MeshLab or Point Cloud Library (both available under GNU General Public Licenses). In further embodiments, the registering procedure 340 may include registering the cylinder 430 to the cropped model 428 using techniques other than an iterative closest point procedure.

The correction procedure 360 includes an operation 362, which involves determining a correction angle 363 corresponding to the angle through which the model 400 is rotated to achieve the target orientation 317. The correction angle 363 may be generated based at least in part upon the registration information 347. In certain forms, the operation 362 may include determining the correction angle 363 based upon a comparison of the initial cylinder 430 and the registered cylinder 440. For example, the operation 362 may include determining the correction angle 363 by determining the angle between the longitudinal axes 431 of the initial cylinder 430 and the registered cylinder 440. In certain forms, the operation 362 may include determining the correction angle 363 based upon the rotation matrices 355R generated during the registering procedure 340. For example, the correction angle 363 may be generated based upon the total rotation matrix 348, or may be defined as a correction rotation matrix 365 corresponding to the total rotation matrix 348.

Figure 10:
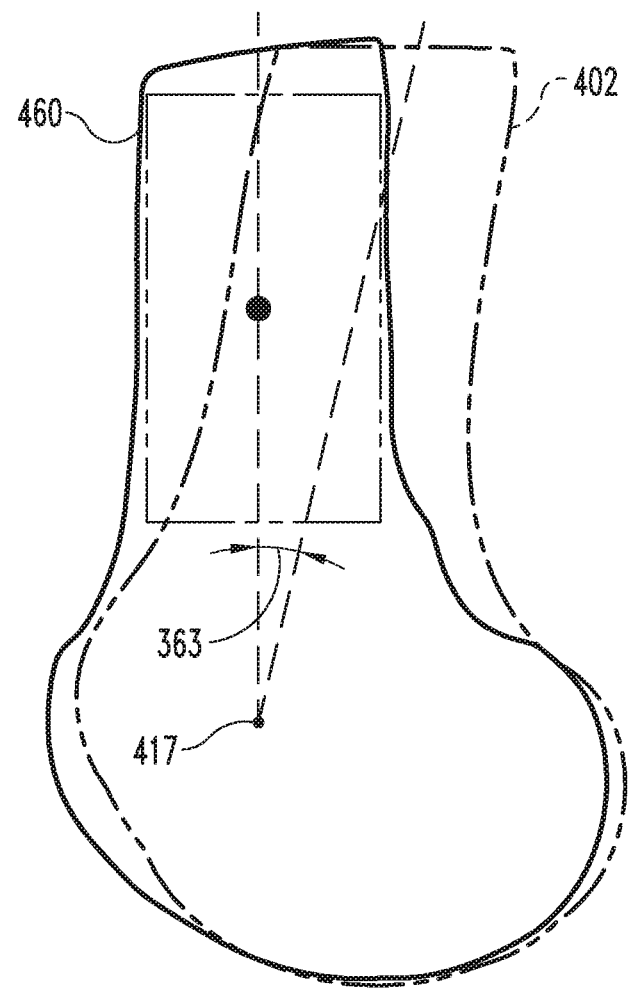
FIG. 10 is a sagittal illustration of an adjusted model of the distal end portion of the femur.

The correction procedure 360 may further include an operation 366, which includes generating a corrected femur model 460 and associated corrected femur model information 367. The operation 366 may include rotating the distal end portion model 402 to generate the corrected femur model 460. In certain embodiments, the operation 366 may include rotating the distal end portion model 402 about the transepicondylar axis 417 by the flexion correction angle 363 to obtain the corrected model 460, for example as illustrated in FIG. 10. In certain embodiments, the operation 366 may include applying the correction rotation matrix 365 to the distal end portion model 402 to generate the corrected model 460. For example, when the correction angle 363 is defined as the total rotation matrix 348 described above, the operation 366 may include applying the total rotation matrix 348 to the distal end portion model 402.

With the corrected model 460 generated, the process 300 may continue to an adjustment procedure 370, which generally involves generating an adjusted model 470 based upon the corrected model 460. The procedure 370 includes an operation 372, which includes determining at least one axis 373 of the femur 100. By way of example, the operation 372 may include determining one or more of the anterior-posterior axis, the transepicondylar axis 117, the posterior condylar axis 118, the anatomic axis 124, and a mechanical axis of the femur 100. In certain forms, the at least one axis 373 may be determined using manual and/or automated techniques known in the art, which need not be described in detail herein. By way of example, the operation 372 may include determining the at least one axis 373 based upon model landmarks, such as the model landmarks 323 identified in the operation 322.

The adjustment procedure 370 further includes an operation 374, which includes rotating the corrected model 460 about the at least one axis 373 to generate the adjusted model 470. For example, the at least one axis 373 may include the anterior-posterior axis, and the operation 374 may include rotating the corrected model 460 about the anterior-posterior axis to adjust the varus-valgus angle for the femur 100. As another example, the at least one axis 373 may include the transepicondylar axis 117, and the operation 374 may include rotating the corrected model 460 about the transepicondylar axis 117 to adjust the neutral flexion angle for the femur 100. As another example, the at least one axis 373 may include the anatomic axis 124, and the operation 374 may include rotating the corrected model about the anatomic axis to adjust the angle for the femur 100. Thus, by rotating the corrected model 460 about the one or more axes 373 to generate the adjusted model 470, the adjusted model 470 may be generated to represent a target post-operative orientation of the femur 100.

As noted above, the process 300 may further include a surgical device procedure 380, which generally involves designing and optionally manufacturing a patient-specific surgical device 387. By way of example, the surgical device 387 may be a cutting block or a femoral prosthesis. The procedure 380 may include an operation 382, which includes generating resection plane information 383 based upon the adjusted model 470 and the at least one axis 373. The resection plane information 383 relates to at least one resection cut to be performed on the distal femur 110 during a surgical procedure, such as a total knee arthroplasty (TKA) procedure. The resection plane information 383 may include information relating to the orientation of the one or more resection planes in relation to the adjusted model 470. In certain forms, the at least one resection plane may be determined using manual and/or automated techniques known in the art, which need not be described in detail herein.

The procedure 380 also includes an operation 384, which includes generating a surgical device model 385 based at least in part upon the resection plane information 383. In certain forms, generation of the surgical device model 385 may be further based upon the adjusted model 470. For example, the surgical device model 385 may be a model of a patient-specific cutting block, and the operation 384 may include generating the cutting block model 385 with cutting slots aligned with the at least one resection plane identified in the operation 382. In such forms, the operation 384 may further include generating the cutting block model 385 with contact surfaces contoured to match the medial condyle 111, the lateral condyle 112 and/or the trochlea 113, which contact surfaces may be generated based upon the corresponding portions of the adjusted femur model 470. As another example, the surgical device model 385 may be a model of a patient-specific femoral prosthesis, and the operation 384 may include generating the femoral prosthesis model 385 with bone-facing surfaces corresponding to the at least one resection plane identified in the operation 382. In such forms, the operation 384 may further include generating the femoral prosthesis model 385 with an outer surface corresponding to the outer surface of a portion of the adjusted femur model 470.

The procedure 380 may further include an operation 386, which includes manufacturing the patient-specific surgical device 387 according to the surgical device model 385. In certain forms, the operation 386 may include generating a mold corresponding to the model 385, and manufacturing the surgical device 387 using the mold, for example using injection-molding or casting techniques. In certain forms, the operation 386 may include manufacturing the surgical device 387 using a rapid manufacturing technique, such as additive manufacturing. By way of example, the operation 386 may include manufacturing the surgical device 387 using a three-dimensional printing technique, for example when the surgical device 387 is an orthopedic cutting block such as a femoral cutting block. As another example, the operation 386 may include manufacturing the surgical device 387 using a selective laser sintering technique, for example when the surgical device 387 is an orthopedic prosthesis such as a femoral prosthesis.

It is to be appreciated that one or more of the operations in the process 300 may include outputting image information for display and inspection by the user, such as at the display device 216. As noted above, FIGS. 4-10 illustrate exemplary stages of the process 300. In certain forms, images corresponding to one or more of the Figures may be output to the display device 216 at an appropriate time during the process 300. In other embodiments, one or more of the intermediate stages may not necessarily be displayed to the user. For example, the cropping planes 426 may or may not be displayed during the operation 326, and the cropped model 428 may or may not be displayed during the operation 328. Furthermore, "generating" a feature need not include generating image data relating to the feature, and may instead include calculating values, equations, or other parameters related to the feature. For example, the operation 334 may include determining equations describing the planes 434, and generating the intersections 435 based upon the equations and the cropped model 428.

While the process 300 has been described and illustrated with reference to a femur 100, the process 300 may also be utilized in connection with other long bones. As will be readily recognized by those having skill in the orthopedic arts, the term "long bones" refers to those bones which are characterized by an elongated diaphysis positioned between two epiphyseal regions. In the human anatomy, long bones include but are not limited to the femur, the tibia, the fibula, the radius, the ulna, and the humerus. It is therefore to be appreciated that alternative embodiments of the process 300 may be utilized to generate correction angles and/or corrected models for one or more of these forms of long bone. By way of example, such a modification may include selecting model landmarks 323 from which the anatomical or mechanical axis of the long bone may be determined, and generating an axis vector 424 based upon such landmarks.

In order to evaluate the accuracy of the above-described technique, one implementation of the process 300 was performed to calculate a correction angle 363 for each of thirty-two different femoral models 400. Additionally, two experts independently determined a flexion correction angle for each model 400 twice, with a waiting period of at least two weeks between tests. Thus, for each model 400, one automated correction angle 363 and four manual correction angles were obtained. Using this data, two additional analyses were performed for each case. A first analysis included comparing the automated correction angle 363 to the average of the four expert correction angles. In this analysis, the mean absolute difference between the automated correction angles 363 and the average of the corresponding expert correction angles was 0.77°.

The second analysis included determining a range of target correction angles based upon the expert correction angles, and determining the accuracy of the automated correction angle 363 based upon the range. More specifically, the accuracy of the automated correction angle 363 was assessed with respect to three margins: within two degrees (2°) of the range, within one degree (1°) of the range, and within zero degrees (0°) the range. In this analysis, all thirty-two of the automated correction angles 363 fell within two degrees (2°) of the expert correction angle range, twenty-seven of the automated correction angles 363 fell within one degree (1°) of the expert correction angle range, and twelve of the automated correction angles 363 fell within zero degrees (0°) of the expert correction angle range.

As is evident from the preliminary results described above, the implemented embodiment of the process 300 was able to achieve results comparable to those obtained manually by experts. Thus, the process 300 may be utilized to streamline the pre-operative planning process by at least partially automating the determination of the correction angle. In certain embodiments, the automated correction angle 363 may be utilized as an initial estimate for the correction angle, and the surgeon may manually adjust the correction angle according to his or her preference and/or professional judgment, for example by manipulating the corrected model 460 using the design tool 220. In either case, the process 300 may reduce the amount of time required to determine a correction angle while increasing consistency by reducing intra-operator and inter-operator variability.

Figure 11:
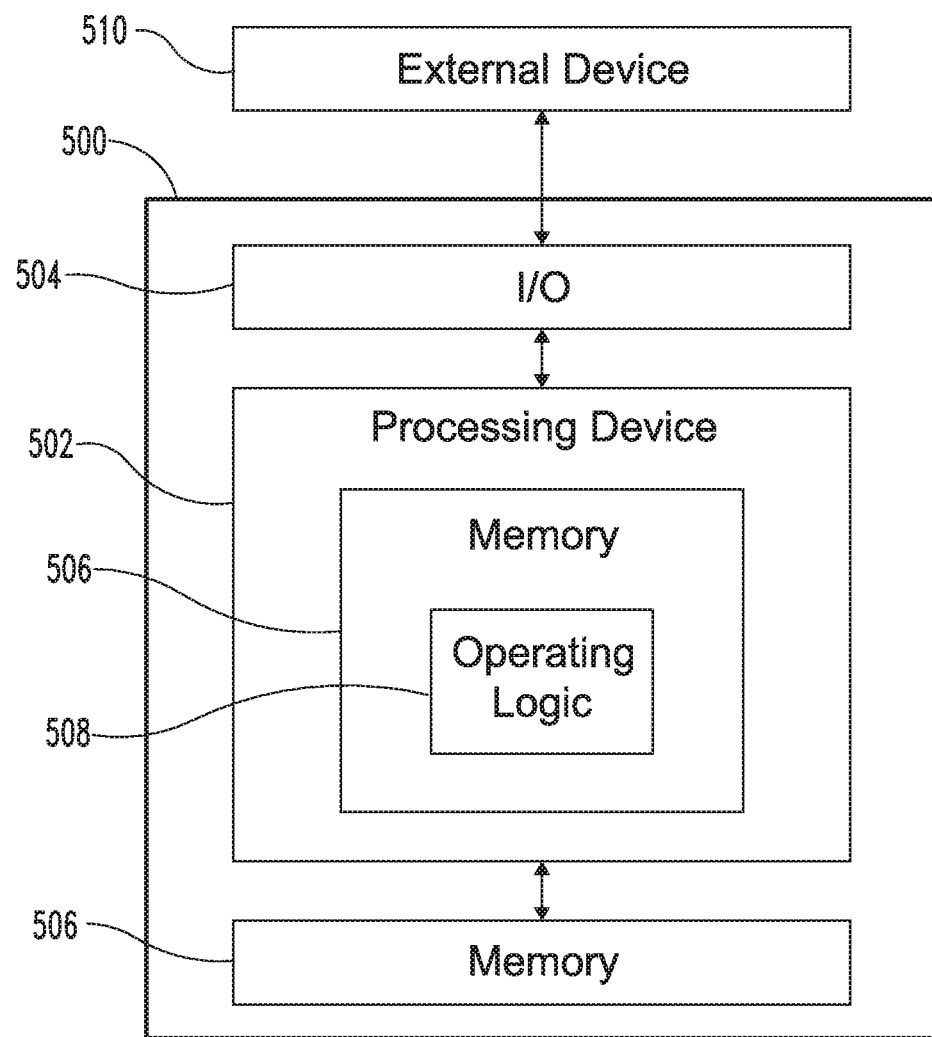
FIG. 11 is a schematic block diagram of a computing device which may be utilized in connection with certain embodiments.

FIG. 11 is a schematic block diagram of a computing device 500. The computing device 500 is one example of a computer, server, mobile device, or equipment configuration which may be utilized in connection with the design device 210, design tools 220, server 240, or modeling tools 250 illustrated in FIG. 2. The computing device 500 includes a processing device 502, an input/output device 504, memory 506, and operating logic 508. Furthermore, the computing device 500 communicates with one or more external devices 510.

The input/output device 504 allows the computing device 500 to communicate with the external device 510. For example, the input/output device 504 may be a network adapter, network card, interface, or a port (e.g., a USB port, serial port, parallel port, an analog port, a digital port, VGA, DVI, HDMI, FireWire, CAT 5, or any other type of port or interface). The input/output device 504 may be comprised of hardware, software, and/or firmware. It is contemplated that the input/output device 504 may include more than one of these adapters, cards, or ports.

The external device 510 may be any type of device that allows data to be inputted or outputted from the computing device 500. For example, the external device 510 may be a mobile device, a reader device, equipment, a handheld computer, a diagnostic tool, a controller, a computer, a server, a printer, a display, an alarm, an illuminated indicator such as a status indicator, a keyboard, a mouse, or a touch screen display. Furthermore, it is contemplated that the external device 510 may be integrated into the computing device 500. It is further contemplated that there may be more than one external device in communication with the computing device 500.

The processing device 502 can be of a programmable type, a dedicated, hardwired state machine, or a combination of these; and can further include multiple processors, Arithmetic-Logic Units (ALUs), Central Processing Units (CPUs), Digital Signal Processors (DSPs) or the like. For forms of processing device 502 with multiple processing units, distributed, pipelined, and/or parallel processing can be utilized as appropriate. The processing device 502 may be dedicated to performance of just the operations described herein or may be utilized in one or more additional applications. In the depicted form, the processing device 502 is of a programmable variety that executes algorithms and processes data in accordance with operating logic 508 as defined by programming instructions (such as software or firmware) stored in memory 506. Alternatively or additionally, the operating logic 508 for processing device 502 is at least partially defined by hardwired logic or other hardware. The processing device 502 can be comprised of one or more components of any type suitable to process the signals received from input/output device 504 or elsewhere, and provide desired output signals. Such components may include digital circuitry, analog circuitry, or a combination of both.

The memory 506 may be of one or more types, such as a solid-state variety, electromagnetic variety, optical variety, or a combination of these forms. Furthermore, the memory 506 can be volatile, nonvolatile, or a combination of these types, and some or all of memory 506 can be of a portable variety, such as a disk, tape, memory stick, cartridge, or the like. In addition, the memory 506 can store data that is manipulated by the operating logic 508 of the processing device 502, such as data representative of signals received from and/or sent to the input/output device 504 in addition to or in lieu of storing programming instructions defining the operating logic 508, to name just one example. As shown in FIG. 11, the memory 506 may be included with the processing device 502 and/or coupled to the processing device 502.

The processes in the present application may be implemented in the operating logic 508 as operations by software, hardware, artificial intelligence, fuzzy logic, or any combination thereof, or at least partially performed by a user or operator. In certain embodiments, units represent software elements as a computer program encoded on a non-transitory computer readable medium, wherein the design device 210, design tool 220, server 240, or modeling tool 250 performs the described operations when executing the computer program.

Certain embodiments of the present disclosure relate to a computer-implemented method comprising: receiving at a computing device information relating to a long bone of a particular patient, wherein the long bone includes a shaft; based upon the received information, generating by the computing device a bone model representative of at least a portion of the long bone, the bone model including a shaft model representative of at least a portion of the shaft; determining with the computing device a target orientation for the bone model; identifying with the computing device a plurality of model landmarks on the bone model, wherein each of the model landmarks corresponds to an anatomical landmark of the long bone; generating by the computing device an axis vector based upon at least one of the model landmarks, wherein the axis vector is representative of an axis of the long bone; generating by the computing device a cropped model based at least in part upon the axis vector, wherein the cropped model includes at least a portion of the shaft model; generating by the computing device a cylinder corresponding to the cropped model; generating by the computing device a registration model comprising a reference model and a source model, wherein the reference model includes one of the cropped model and the cylinder, and wherein the source model includes the other of the cropped model and the cylinder; generating by the computing device a registered model based upon the registration model, wherein generating the registered model includes registering the source model to the reference model; generating by the computing device registration information relating to the registering; generating by the computing device a correction angle based upon the registration information; and generating by the computing device a corrected bone model, wherein generating the corrected bone model includes applying the correction angle to the bone model.

In certain embodiments, generating a cylinder corresponding to the cropped model includes determining a radius based upon the cropped model, determining a longitudinal axis orientation based upon the target orientation, and generating the cylinder with the radius and a longitudinal axis, wherein the longitudinal axis has the longitudinal axis orientation with respect to the axis vector.

In certain embodiments, generating the registration model further includes generating point clouds, and generating the point clouds includes generating a reference point cloud for the reference model and generating a source point cloud for the source model.

In certain embodiments, registering the source model to the reference model includes performing a plurality of iterations of a movement procedure, and each iteration of the movement procedure comprises: generating nearest neighbor information for the registration model, the nearest neighbor information associates each point in the source point cloud with a nearest neighbor point in the reference point cloud; generating a movement parameter which, when applied to the source model, increases a correlation between points associated with one another by the nearest neighbor information; and updating the source model and the source point cloud, and updating the source model and the source point cloud includes applying the movement parameter to the source model and the source point cloud.

In certain embodiments, the registration information relates to a total movement parameter corresponding to a combination of the movement parameters generated in the plurality of iterations of the movement procedure.

In certain embodiments, generating the correction angle includes generating a correction movement parameter based upon the total movement parameter, and applying the correction angle to the bone model includes applying the correction movement parameter to the bone model.

In certain embodiments, the method further comprises generating a first cropping plane and a second cropping plane, each of the cropping planes intersects the bone model and the axis vector, and generating the cropped model includes cropping the bone model based upon the cropping planes.

In certain embodiments, the received information relates to diagnostic imaging data representative of the long bone, generating the bone model includes generating the bone model based upon the diagnostic imaging data, the method further comprises identifying a region of the diagnostic imaging data based upon a fidelity of the region, the method further comprises identifying a portion of the bone model corresponding to the identified region of the diagnostic imaging data, and at least one of the cropping planes is generated based at least in part upon the identified portion of the bone model.

In certain embodiments, the diagnostic imaging data is generated using a diagnostic imaging technique, identifying the region of the diagnostic imaging data based upon the fidelity of the region includes identifying the region based upon empirical data related to fidelity of the diagnostic imaging technique in the region.

In certain embodiments, the received information relates to diagnostic imaging data representative of the long bone, generating the bone model includes generating the bone model based upon the diagnostic imaging data, the diagnostic imaging data represents the long bone with varying fidelity, and generating the cropped model includes generating the cropped model based at least in part upon fidelity of the diagnostic imaging data.

In certain embodiments, the received information relates to diagnostic imaging data representative of the long bone, the diagnostic imaging data includes a higher-fidelity region and a lower-fidelity region, generating the bone model includes generating the bone model based upon the diagnostic imaging data, the bone model includes a first portion corresponding to the higher-fidelity region of the diagnostic imaging data and a second portion corresponding to the lower-fidelity region of the diagnostic imaging data, and the cropped model includes the first portion and excludes the second portion.

Certain embodiments of the present disclosure relate to a method comprising: receiving patient information relating to a long bone of a particular patient, wherein the long bone includes a shaft; based upon the patient information, generating a bone model representative of at least a portion of the long bone, wherein the bone model includes a shaft model representative of at least a portion of the shaft of the long bone; defining a target orientation for the bone model; generating a plurality of model landmarks for the bone model, wherein each of the model landmarks is representative of an anatomical landmark of the long bone; based upon at least one of the model landmarks, generating an axis vector representative of an axis of the long bone; based at least in part upon the axis vector, generating a pair of cropping planes, wherein each of the cropping planes intersects the axis vector and the bone model, and wherein a portion of the bone model is located between the cropping planes; cropping the bone model at the cropping planes, thereby generating a cropped model corresponding to the portion of the bone model located between the cropping planes; determining a plurality of cylinder parameters, wherein determining the plurality of cylinder parameters comprises determining a cylinder radius based upon the cropped model and determining a longitudinal axis orientation based upon the target orientation; based upon the plurality of cylinder parameters, generating a cylinder having the cylinder radius and the longitudinal axis orientation; generating a registration model comprising a reference model and a source model, wherein the reference model includes one of the cropped model and the cylinder, and wherein the source model includes the other of the cropped model and the cylinder; generating a reference point cloud on the reference model; generating a source point cloud on the source model; performing at least one iteration of a movement procedure, wherein each iteration of the movement procedure comprises: generating a movement parameter which, when applied to the source model, increases a correlation between the source point cloud and the reference point cloud; applying the movement parameter to the cylinder and the source point cloud, thereby updating the registration model; generating an iteration criterion related to at least one feature of the iteration; determining whether or not to perform an additional iteration based upon the iteration criterion and a comparison criterion; in response to determining to perform the additional iteration, performing the additional iteration; and in response to determining not to perform the additional iteration, generating a registered model corresponding to the updated registration model; generating registration information relating to a difference between the initial registration model and the registered model; determining a correction angle based at least in part upon the registration information; and generating a corrected bone model, wherein generating the corrected bone model includes applying the correction angle to the bone model.

In certain embodiments, performing at least one iteration of the movement procedure comprises performing a plurality of the iterations, the movement parameter comprises a rotation matrix, and generating the registration information includes combining the rotation matrices generated in the plurality of iterations, thereby generating a total rotation matrix.

In certain embodiments, the correction angle includes the total rotation matrix, and applying the correction angle to the bone model includes applying the total rotation matrix to the bone model.

In certain embodiments, generating the registration information comprises determining an offset angle between a longitudinal axis of the source model of the initial registration model and a longitudinal axis of the source model of the registered model, and determining the correction angle includes determining the correction angle based upon the offset angle.

In certain embodiments, the patient information comprises diagnostic imaging information, and generating the bone model includes generating the bone model based upon the diagnostic imaging information.

In certain embodiments, the diagnostic imaging information comprises magnetic resonance imaging (MM) information relating to an MRI image set, the MRI image set has a border, the bone model has an end corresponding to the border, the method further comprises defining an offset region adjacent the end of the model, and generating the pair of cropping planes includes generating each of the cropping planes outside of the offset region.

In certain embodiments, the offset region is defined based upon information relating to fidelity of the MRI image set in regions adjacent the border.

In certain embodiments, generating the bone model includes generating the bone model in a virtual three-dimensional space having a coordinate system, and defining the target orientation for the bone model includes defining the target orientation based upon the coordinate system.

In certain embodiments, defining the target orientation based upon the coordinate system includes defining the target orientation parallel to an axis of the coordinate system.

In certain embodiments, generating the movement parameter includes generating the movement parameter based upon an estimate of an optimal value for the movement parameter, wherein the optimal value for the movement parameter maximizes the correlation between the source point cloud and the reference point cloud when applied to the source model.

In certain embodiments, each iteration of the movement procedure further comprises generating nearest neighbor information associating each point in the source point cloud with a nearest point in the reference point cloud, and the correlation between the source point cloud and the reference point cloud relates to an average distance between points associated by the nearest neighbor information.

In certain embodiments, the average distance is one of a mean absolute distance and a root mean square average distance.

In certain embodiments, defining the target orientation includes defining the target orientation based upon the patient information.

In certain embodiments, the patient information includes information relating to an axis of the anatomy of the particular patient, and defining the target orientation based upon the patient information includes defining the target orientation based upon the information relating to the axis of the anatomy of the particular patient.

In certain embodiments, the patient information includes model information relating to the bone model, and the model information is based upon diagnostic imaging information.

In certain embodiments, the long bone is a femur, the shaft is a femoral shaft, the shaft axis is an anatomical axis of the femur, and the bone model is representative of a distal end portion of the femur.

In certain embodiments, the method further comprises generating an adjusted femur model, wherein generating the adjusted femur model includes determining at least one axis of the corrected bone model, and rotating the corrected bone model about each of the at least one axes.

In certain embodiments, the method further comprises determining at least one resection plane based upon the at least one axis, and generating a surgical tool model based at least in part upon the at least one resection plane.

In certain embodiments, the at least one axis includes at least one of an anterior-posterior axis, a transepicondylar axis, and a posterior condylar axis.

In certain embodiments, the surgical tool model is a cutting block model, and generating the cutting block model includes generating the cutting block model with at least one cutting slot aligned with the at least one resection plane.

In certain embodiments, the surgical tool model is a femoral prosthesis model, and generating the femoral prosthesis model includes generating the femoral prosthesis model with at least one bone-facing surface corresponding to the at least one resection plane.

In certain embodiments, the method further comprises manufacturing the surgical tool based upon the surgical tool model.

In certain embodiments, manufacturing the surgical tool includes manufacturing the tool using a rapid manufacturing technique.

Certain embodiments of the present disclosure relate to a method comprising: receiving patient information relating to a long bone of a particular patient, wherein the long bone includes a diaphysis, wherein the patient information includes diagnostic imaging information representative of at least a portion of the long bone, and wherein the at least a portion of the long bone includes at least a portion of the diaphysis; receiving fidelity information relating to fidelity of the diagnostic imaging information, the fidelity information indicating a higher-fidelity region of the diagnostic imaging information and at least one lower-fidelity region of the diagnostic imaging information, wherein the higher-fidelity region represents a corresponding portion of the diaphysis with a higher fidelity, and wherein each lower-fidelity region represents a corresponding portion of the diaphysis with a lower fidelity; based upon the received information, generating a bone model representative of the at least a portion of the long bone, the bone model including a shaft model representative of the at least a portion of the diaphysis; determining a shaft model axis, the shaft model axis corresponding to a longitudinal axis of the shaft model; defining a target orientation for the shaft model axis; identifying a first portion of the shaft model corresponding to the higher-fidelity region of the diagnostic imaging information; identifying at least one second portion of the shaft model corresponding to the at least one lower-fidelity region of the diagnostic imaging information; generating a cropped model including the first portion of the shaft model, wherein generating the cropped model includes cropping the at least one second portion of the shaft model from the bone model; determining an average radius of the shaft model with respect to the shaft model axis; generating a cylinder having a cylinder radius and a cylinder axis, wherein the cylinder radius corresponds to the average radius of the shaft model, and wherein the cylinder axis corresponds to the target orientation for the shaft model axis; generating a registration model comprising a reference model and a source model, wherein the reference model includes one of the cropped model and the cylinder, and wherein the source model includes the other of the cropped model and the cylinder; generating a registered model based upon the registration model, wherein generating the registered model includes registering the source model to the reference model, and wherein registering the source model to the reference model includes determining a movement parameter and applying the movement parameter to the source model; and generating a corrected bone model, wherein generating the corrected bone model includes applying at least a portion of the movement parameter to the bone model.

In certain embodiments, registering the source model to the reference model includes performing an iterative closest points procedure comprising a plurality of iterative procedures; each of the iterative procedures comprises determining an iterative movement parameter which increases a correlation between the source model and the reference model and applying the iterative movement parameter to the source model; determining the movement parameter includes iteratively determining the iterative movement parameters; and applying the movement parameter to the source model includes iteratively applying the iterative movement parameters to the source model.

In certain embodiments, the movement parameter includes a rotation parameter and a translation parameter, and applying at least a portion of the movement parameter to the bone model includes applying at least the rotation parameter to the bone model.

In certain embodiments, the at least a portion of the long bone further includes an epiphysis, the bone model further includes an epiphyseal model representative of the epiphysis, and generating the cropped model further includes cropping the epiphyseal model from the bone model.

In certain embodiments, the shaft model includes a first end portion adjacent the epiphyseal model, and a first of the at least one second portions of the shaft model includes the first end portion of the shaft model.

In certain embodiments, the shaft model further includes a second end portion corresponding to a boundary region of the diagnostic imaging information, and a second of the at least one second portions of the shaft model includes the second end portion of the shaft model.

In certain embodiments, the diagnostic imaging information is generated using a particular imaging technique, and the fidelity information includes empirical information relating to fidelity of imaging information generated using the particular imaging technique.

In certain embodiments, a first of the at least one lower-fidelity regions is located adjacent a border of the diagnostic imaging information.

In certain embodiments, the first lower-fidelity region is located between the border and the higher-fidelity region.

In certain embodiments, the higher-fidelity region is located between the first lower-fidelity region and a second of the at least one lower fidelity regions.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A computer-implemented method, comprising:
receiving at a computing device information relating to a long bone of a particular patient, wherein the long bone includes a shaft;
based upon the received information, generating by the computing device a bone model representative of at least a portion of the long bone, the bone model including a shaft model representative of at least a portion of the shaft;
determining with the computing device a target orientation for the bone model;
identifying with the computing device a plurality of model landmarks on the bone model, wherein each of the model landmarks corresponds to an anatomical landmark of the long bone;
generating by the computing device an axis vector based upon at least one of the model landmarks, wherein the axis vector is representative of an axis of the long bone;
generating by the computing device a cropped model based at least in part upon the axis vector, wherein the cropped model includes at least a portion of the shaft model;

generating by the computing device a cylinder corresponding to the cropped model;
generating by the computing device a registration model comprising a reference model and a source model, wherein the reference model includes one of the cropped model and the cylinder, and wherein the source model includes the other of the cropped model and the cylinder;
generating by the computing device a registered model based upon the registration model, wherein generating the registered model includes registering the source model to the reference model;
generating by the computing device registration information relating to the registering;
generating by the computing device a correction angle based upon the registration information; and
generating by the computing device a corrected bone model, wherein generating the corrected bone model includes applying the correction angle to the bone model.

2. The method of claim 1, wherein generating a cylinder corresponding to the cropped model includes determining a radius based upon the cropped model, determining a longitudinal axis orientation based upon the target orientation, and generating the cylinder with the radius and a longitudinal axis, wherein the longitudinal axis has the longitudinal axis orientation with respect to the axis vector.

3. The method of claim 1, wherein generating the registration model further includes generating point clouds, and wherein generating the point clouds includes generating a reference point cloud for the reference model and generating a source point cloud for the source model.

4. The method of claim 3, wherein registering the source model to the reference model includes performing a plurality of iterations of a movement procedure, each iteration of the movement procedure comprising:
generating nearest neighbor information for the registration model, wherein the nearest neighbor information associates each point in the source point cloud with a nearest neighbor point in the reference point cloud;
generating a movement parameter which, when applied to the source model, increases a correlation between points associated with one another by the nearest neighbor information; and
updating the source model and the source point cloud, wherein updating the source model and the source point cloud includes applying the movement parameter to the source model and the source point cloud.

5. The method of claim 4, wherein the registration information relates to a total movement parameter corresponding to a combination of the movement parameters generated in the plurality of iterations of the movement procedure.

6. The method of claim 5, wherein generating the correction angle includes generating a correction movement parameter based upon the total movement parameter, and wherein applying the correction angle to the bone model includes applying the correction movement parameter to the bone model.

7. The method of claim 1, further comprising generating with the computing device a first cropping plane and a second cropping plane, wherein each of the cropping planes intersects the bone model and the axis vector, and wherein generating the cropped model includes cropping the bone model based upon the cropping planes.

8. The method of claim 7, wherein the received information relates to diagnostic imaging data representative of the long bone, wherein generating the bone model includes generating the bone model based upon the diagnostic imaging data, wherein the method further comprises identifying with the computing device a region of the diagnostic imaging data based upon a fidelity of the region, wherein the method further comprises identifying with the computing device a portion of the bone model corresponding to the identified region of the diagnostic imaging data, and wherein at least one of the cropping planes is generated based at least in part upon the identified portion of the bone model.

9. The method of claim 8, wherein the diagnostic imaging data is generated using a diagnostic imaging technique, wherein identifying the region of the diagnostic imaging data based upon the fidelity of the region includes identifying the region based upon empirical data related to fidelity of the diagnostic imaging technique in the region.

10. The method of claim 1, wherein the received information relates to diagnostic imaging data representative of the long bone, wherein generating the bone model includes generating the bone model based upon the diagnostic imaging data, wherein the diagnostic imaging data represents the long bone with varying fidelity, and wherein generating the cropped model includes generating the cropped model based at least in part upon fidelity of the diagnostic imaging data.

11. The method of claim 1, wherein the received information relates to diagnostic imaging data representative of the long bone, wherein the diagnostic imaging data includes a higher-fidelity region and a lower-fidelity region, wherein generating the bone model includes generating the bone model based upon the diagnostic imaging data, wherein the bone model includes a first portion corresponding to the higher-fidelity region of the diagnostic imaging data and a second portion corresponding to the lower-fidelity region of the diagnostic imaging data, and wherein the cropped model includes the first portion and excludes the second portion.

12. A method, comprising:
receiving patient information relating to a long bone of a particular patient, wherein the long bone includes a shaft;
based upon the patient information, generating a bone model representative of at least a portion of the long bone, wherein the bone model includes a shaft model representative of at least a portion of the shaft of the long bone;
defining a target orientation for the bone model;
generating a plurality of model landmarks for the bone model, wherein each of the model landmarks is representative of an anatomical landmark of the long bone;
based upon at least one of the model landmarks, generating an axis vector representative of an axis of the long bone;
based at least in part upon the axis vector, generating a pair of cropping planes, wherein each of the cropping planes intersects the axis vector and the bone model, and wherein a portion of the bone model is located between the cropping planes;
cropping the bone model at the cropping planes, thereby generating a cropped model corresponding to the portion of the bone model located between the cropping planes;
generating a cylinder corresponding to the cropped model;
generating a registration model comprising a reference model and a source model, wherein the reference model includes one of the cropped model and the cylinder, and wherein the source model includes the other of the cropped model and the cylinder;
generating a reference point cloud on the reference model;

generating a source point cloud on the source model;
performing at least one iteration of a movement procedure, wherein each iteration of the movement procedure comprises:
  generating a movement parameter which, when applied to the source model, increases a correlation between the source point cloud and the reference point cloud;
  applying the movement parameter to the cylinder and the source point cloud, thereby updating the registration model;
  generating an iteration criterion related to at least one feature of the iteration;
  determining whether or not to perform an additional iteration based upon the iteration criterion and a comparison criterion;
  in response to determining to perform the additional iteration, performing the additional iteration; and
  in response to determining not to perform the additional iteration, generating a registered model corresponding to the updated registration model;
generating registration information relating to a difference between the initial registration model and the registered model;
determining a correction angle based at least in part upon the registration information; and
generating a corrected bone model, wherein generating the corrected bone model includes applying the correction angle to the bone model.

13. The method of claim 12, wherein generating a cylinder corresponding to the cropped model includes determining a plurality of cylinder parameters and generating the cylinder based upon the cylinder parameters; wherein determining the plurality of cylinder parameters comprises determining a cylinder radius based upon the cropped model, and determining a longitudinal axis orientation based upon the target orientation; and wherein generating the cylinder based upon the cylinder parameters includes generating the cylinder with the cylinder radius and the longitudinal axis orientation.

14. The method of claim 12, wherein performing at least one iteration of the movement procedure comprises performing a plurality of the iterations, wherein the movement parameter comprises a rotation matrix, and wherein generating the registration information includes combining the rotation matrices generated in the plurality of iterations, thereby generating a total rotation matrix.

15. The method of claim 14, wherein the correction angle corresponds to the total rotation matrix, and wherein applying the correction angle to the bone model includes applying the total rotation matrix to the bone model.

16. The method of claim 12, wherein generating the registration information comprises determining an offset angle between a longitudinal axis of the source model of the initial registration model and a longitudinal axis of the source model of the registered model, and wherein determining the correction angle includes determining the correction angle based upon the offset angle.

17. The method of claim 12, wherein the patient information comprises diagnostic imaging information, and wherein generating the bone model includes generating the bone model based upon the diagnostic imaging information.

18. The method of claim 17, wherein the diagnostic imaging information comprises magnetic resonance imaging (MRI) information relating to an MRI image set, wherein the MRI image set has a border, wherein the bone model has an end corresponding to the border, wherein the method further comprises defining an offset region adjacent the end of the model, and wherein generating the pair of cropping planes includes generating each of the cropping planes outside of the offset region.

19. The method of claim 18, wherein the offset region is defined based upon information relating to fidelity of the MRI image set in regions adjacent the border.

20. The method of claim 12, wherein generating the bone model includes generating the bone model in a virtual three-dimensional space having a coordinate system, and wherein defining the target orientation for the bone model includes defining the target orientation based upon the coordinate system.

21. The method of claim 12, wherein generating the movement parameter includes generating the movement parameter based upon an estimate of an optimal value for the movement parameter, wherein the optimal value for the movement parameter maximizes the correlation between the source point cloud and the reference point cloud when applied to the source model.

22. The method of claim 12, wherein each iteration of the movement procedure further comprises generating nearest neighbor information associating each point in the source point cloud with a nearest point in the reference point cloud, and wherein the correlation between the source point cloud and the reference point cloud relates to an average distance between points associated by the nearest neighbor information.

23. The method of claim 12, wherein defining the target orientation includes defining the target orientation based upon the patient information.

24. The method of claim 22, wherein the patient information includes information relating to an axis of the anatomy of the particular patient, and wherein defining the target orientation based upon the patient information includes defining the target orientation based upon the information relating to the axis of the anatomy of the particular patient.

25. The method of claim 12, wherein the patient information includes model information relating to the bone model, and wherein the model information is based upon diagnostic imaging information.

* * * * *